(12) United States Patent
Naso et al.

(10) Patent No.: US 11,951,078 B2
(45) Date of Patent: *Apr. 9, 2024

(54) METHOD FOR PREVENTING THE FORMATION OF CALCIFIED DEPOSITS AND FOR INACTIVATING XENOANTIGENS IN BIOLOGICAL MATRICES

(71) Applicant: BIOCOMPATIBILITY INNOVATION S.R.L., Padua (IT)

(72) Inventors: Filippo Naso, Padua (IT); Alessandro Gandaglia, Padua (IT)

(73) Assignee: BIOCOMPATIBILITY INNOVATION S.R.L., Padua (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,154

(22) Filed: May 22, 2020

(65) Prior Publication Data

US 2020/0368178 A1 Nov. 26, 2020

Related U.S. Application Data

(60) Provisional application No. 62/851,194, filed on May 22, 2019.

(51) Int. Cl.
*A61K 31/05* (2006.01)
*A61K 9/08* (2006.01)
*A61K 31/192* (2006.01)
*A61K 31/216* (2006.01)
*A61K 31/353* (2006.01)
*A61K 31/7024* (2006.01)
*A61K 31/704* (2006.01)

(52) U.S. Cl.
CPC ................. *A61K 31/05* (2013.01); *A61K 9/08* (2013.01); *A61K 31/192* (2013.01); *A61K 31/216* (2013.01); *A61K 31/353* (2013.01); *A61K 31/7024* (2013.01); *A61K 31/704* (2013.01)

(58) Field of Classification Search
CPC ........ A61K 31/05; A61K 9/08; A61K 31/192; A61K 31/216; A61K 31/353; A61K 31/7024; A61K 31/704
USPC .......................................................... 514/32
See application file for complete search history.

(56) References Cited

U.S. PATENT DOCUMENTS

2014/0018909 A1* 1/2014 Simionescu ....... A61K 31/7024
623/1.49

FOREIGN PATENT DOCUMENTS

IT WO 2017/093147 A1 * 6/2017

* cited by examiner

*Primary Examiner* — Yih-Horng Shiao
(74) *Attorney, Agent, or Firm* — Valauskas Corder LLC

(57) ABSTRACT

The present invention discloses a method for preventing the formation of calcified deposits or inside an isolated biological matrix comprising the step of contacting said isolated biological matrix with a solution comprising a mixture of phenolic compounds.

17 Claims, 25 Drawing Sheets

METHOD FOR PREVENTING THE FORMATION OF CALCIFIED DEPOSITS AND FOR INACTIVATING XENOANTIGENS IN BIOLOGICAL MATRICES

CROSS-REFERENCE TO RELATED APPLICATIONS

The present invention claims priority to U.S. Provisional Patent Application No. 62/851,194 filed on May 22, 2019.

BACKGROUND OF THE INVENTION

The present invention finds application in the medical, biomedical or veterinary field and, in particular, in the preparation of biological and biocompatible matrices to be implanted in the human or animal body.

The production of bioprosthetic substitutes is currently undergoing a significant market expansion. The clinical improvement of surgical procedures, the decrease in post-surgical complications, the development and management of new immune-modulating medicine, combined with a more in-depth knowledge of the interaction mechanisms between graft and host, all contribute to facilitating the use of biological prostheses constituted by an animal or homologous tissue. In this sense, one sector that is representative is the cardiovascular sector, especially in terms of the social and health impact that the established practice of cardiac valve replacement can cause.

Biomedical technology is capable of developing and surgically applying valve prostheses for replacement that can imitate the opening and closing function of dysfunctional native valves. A desirable bioprosthetic heart valve substitute (BHV) should be capable of allowing a transvalve flow that can overlap that of the analogue original, healthy valve, to ensure a long lifetime and not generate haemolytic or thrombogenic effects.

The valve substitutes that are most often used are biological prostheses derived from xenogeneic tissues, in particular from pig valves or valves produced with the bovine, equine or porcine pericardium.

Such valve prostheses and substitutes suffer from many criticalities that severely limit their clinical application.

The international patent application WO 2017/093147 discloses a method for the inactivation of xenoantigens, and in particular of alpha-Gal, in biological tissues for the production of bioprostheses. Aspects relating to calcification are incidentally mentioned as proved by the absence of any experimental description supporting its effectiveness.

The US patent application US 2014/018909 discloses a method for preserving tissues intended for applications in the cardiovascular field, from the products of reactions that accumulate in patients with diabetes and, in particular, resulting from the oxidation of lipid components. These catabolic products are named as AGEs and are responsible for accelerating the degeneration mechanisms of bioprosthetic substitutes, such as vessels and heart valves, in diabetic patients. The method is disclosed in connection with Pentagalfoylglucose—PGG, only and it is performed on a collagen matrix obtained by decellularizing a porcine heart valve and an elastin matrix obtained by treating a previously decellularized porcine carotid artery with alkali.

The international patent application WO 01/21228 discloses the use of gallotanic acid to mitigate the calcification of biological or synthetic tissues that can be used for the production of heart valve substitutes.

SUMMARY OF THE INVENTION

The inventors of the present patent application have surprisingly found a method for increasing the biocompatibility of prostheses, particularly of cardiac prostheses. In particular, the increased biocompatibility comprises the increase in one or more of: preventing the formation of calcified deposits, inactivating xenoantigens in biological matrices, preventing the thrombus formation in a biological matrix, preventing the lipid infiltration into a biological matrix, preventing the onset of inflammatory process mediated by the cellular component, prevents the biofouling processes on a biological matrix.

OBJECT OF THE INVENTION

Figure 1:
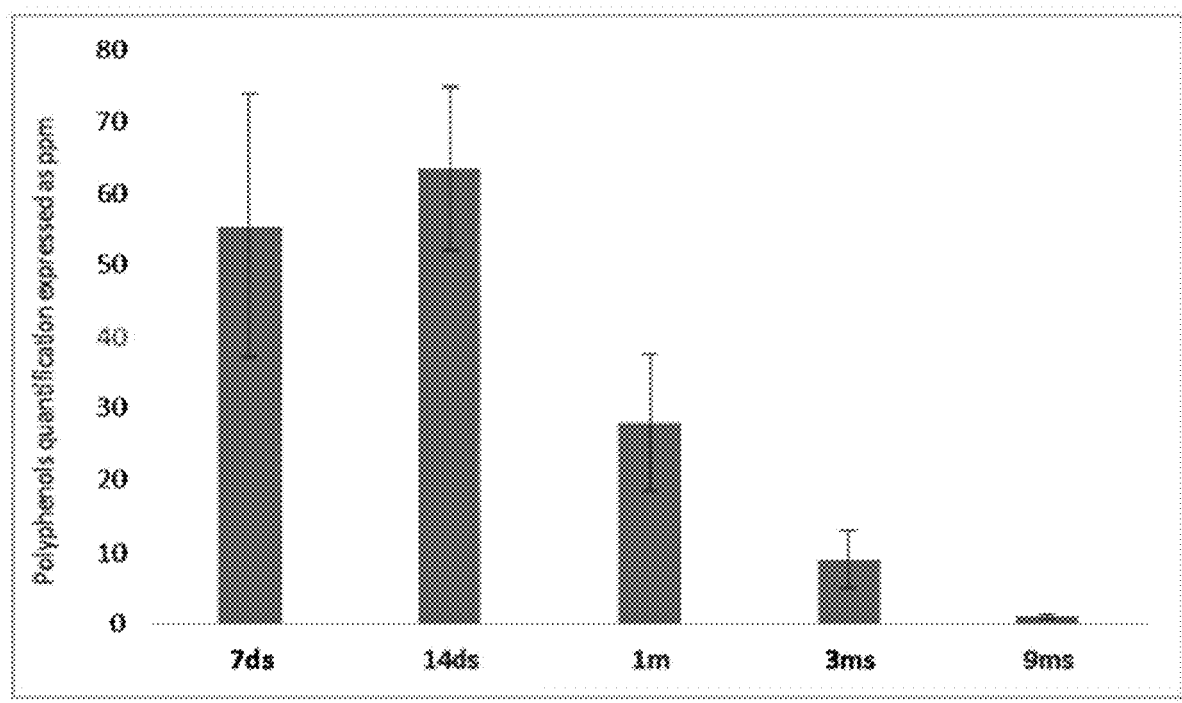
FIG. 1: results of the assays on the phenolic compound release.

In a first object, the present invention discloses a method for preventing the formation of calcified deposits in a biological matrix.

In a preferred embodiment, said method comprises the step of contacting said biological matrix with a solution comprising a mixture of phenolic compounds for a period of fewer than two hours at the temperature of 35±2° C. and in the dark.

According to an aspect of the invention, the method disclosed also inactivates xenoantigens in biological matrices.

According to another aspect of the invention, the method disclosed prevents the thrombus formation on a biological matrix.

According to a further aspect of the invention, the method disclosed prevents the lipid infiltration into a biological matrix.

According to a still further aspect of the invention, the method disclosed prevents the onset of an inflammatory process mediated by the cellular component.

According to another further aspect of the invention, the method disclosed prevents the formation of the microorganism biofilm on a biological matrix (biofouling).

In a preferred embodiment, the method disclosed provides one or more of: preventing the formation of calcified deposits, inactivating xenoantigens in biological matrices, preventing the thrombus formation on a biological matrix, preventing the lipid infiltration into a biological matrix, preventing the onset of inflammatory process mediated by the cellular component, prevents the biofouling processes on a biological matrix.

In a more preferred embodiment, the method disclosed provides for: preventing the formation of calcified deposits, inactivating xenoantigens in biological matrixes, preventing the thrombus formation on a biological matrix, preventing the lipid infiltration into a biological matrix and preventing the onset of inflammatory process mediated by the cellular component, prevents the biofouling processes on a biological matrix.

A biological matrix obtained with the method of the invention is another object of the present application.

A biological matrix obtained with the method of the invention for use in the treatment of heart diseases in the medical, biomedical and/or veterinary field represents a second object of the present application.

In one aspect of the invention, it is disclosed a method for the treatment of heart diseases in humans or animals comprising the use of a biological matrix obtained according to the method of the invention.

A solution comprising a phenolic compound or a mixture of phenolic compounds to be used in the methods of the present patent application represents a further object of the invention.

According to another aspect of the invention, it is disclosed a method for the preparation of the invention solution comprising a mixture of phenolic compounds.

In a further object, the present invention discloses a kit for performing the invention method.

DETAILED DESCRIPTION OF THE INVENTION

According to a first object, the present invention discloses a method for preventing the formation of calcified deposits in a biological matrix.

For the purposes of the present invention, a calcification may occur on the surface of a biological matrix or inside a biological matrix.

For the purposes of the present description, a method according to the invention is referred to as FACTA™.

In particular, said method comprises the step of contacting the said biological matrix with a solution comprising a mixture of phenolic compounds.

For the purposes of the present invention, biological matrices are xenomatrices, i.e. they are not of human origin.

In particular, they can have equine, porcine or bovine origin.

In a preferred embodiment, biological matrices shall be intended as: vessels, cardiac valves, tendons, ligaments, pericardium, muscular fasciae, dura mater, tympanic membrane, intestinal submucosa, cartilages, adipose tissue and bone tissue, pelvic, abdominal and breast tissue.

In a more preferred embodiments, biological matrices are selected in the group comprising cardiovascular prostheses (cardiac valves) and pericardial tissue patches.

An example of such cardiac valve is represented by Trifecta™ Valve with Glide™ Technology and Epic™ Mitral Valve (Abbott/St. Jude Medical, St. Paul, MN, USA).

Other examples for mere explanatory purposes may be Sapien 3, Sapien 3 Ultra and Sapien XT transcatheter heart valve (Edwards Lifesciences, Irvine, CA, USA), Inspiris Resilia, Intuity Valve System, Magna Easy, Perimount RSR and Perimount Valve (Edwards Lifesciences, Irvine, CA, USA), Avalus™, Contegra Valved Conduit, Freestyle™, Hancock II™, Mosaic™ and Mosaic™ Ultra, Melody™ and CoreValve transcatheter valve replacement platform (Medtronic, Minneapolis, MN, USA), Acurate Neo™ and Lotu Edge™ Aortic Valve System (Boston Scientific, Marlborough, MA, USA), Accufit® Transapical Mitral Valve (Sinomed, Tianjin, China), Xinli® (KingstronBio, Jiangsu, China), Bioconduit™, Biomitral™, Biopulmonic™ Conduit and Injectable Biopulmonic™ (BioIntegral, Mississauga, ON, Canada).

In a still preferred embodiment, the cardiac valves which can be treated according to the present invention are represented by trans-catheter implantable heart valves (TAVI); said valves require to be implanted through a catheter and, accordingly, need to be pliable to be housed within the catheter.

For the purposes of the present invention, a phenolic compound within the phenolic compound mixture above referred shall be intended as a phenolic or polyphenolic compound (in some instances used here as synonyms) selected from the group comprising: simple phenols, phenolic aldehydes, phenolic acids, phenylamines, phenol compounds, flavonoids, phenylpropanoids and tannins.

In particular, a phenolic compound is selected in the group comprising: vanillin, cinnamic acids, phenylalanine, coumarins, xanthones, catechins, flavononids, flavones, chalcones, flavanonols, flavanols, leucoanthocyanidin, anthocyanidin, hydroxycinnamic acids, phenylpropanoids.

More in particular, a phenolic compound can be selected in the group comprising: resveratrol, aloin, cyanarin, epigallocatechin, tannic acid, caffeic acid, chlorogenic acid, hydroxytyrosol, rosmarinic acid, narigenin, gallic acid, hesperidin, quinic acid, eleonolic acid, pinoresinol, luteolin, apigenin, tangeritin, isorhamnetin, kaempferol, myricetin, eriodictyol, hesperetin, naringenin, theaflavin, thearubigins, daidzein, genistein, glycitein, pterostilbene, delphinidin, malvidin, pelargonidin, peonidin, chicoric acid, ferulic acid, salicylic acid.

As per one embodiment of the present invention, curcumin can also be used.

For the purposes of the present invention, derivatives of the above disclosed phenolic or polyphenolic compound are also encompassed; for instance, salts or esters may also be used.

In one embodiment of the invention, the solution comprises a mixture of two or more of the above disclosed phenylpropanoids.

Within the solution of the invention, each phenylpropanoid may be present in a concentration comprised between about 0.2-5 mg/ml±0.5 mg/ml (w/total volume of the solution).

Here below there are reported some solutions according to the above disclosure:

| Solution | Compound - quantity (mg/ml) ± 0.5 mg/ml | Compound - quantity (mg/ml) ± 0.5 mg/ml |
| --- | --- | --- |
| A | Resveratrol 3 mg/ml | Aloin 1.5 mg/ml |
| B | Resveratrol 3 mg/ml | Cynarin 2 mg/ml |
| C | Epigallocatechin 2 mg/ml | Aloin 1.5 mg/ml |
| D | Tannic Acid 4 mg/ml | Chlorogenic Acid 4 mg/ml |
| E | Tannic Acid 4 mg/ml | Caffeic Acid 2 mg/ml |
| F | Chlorogenic Acid 4 mg/ml | Hydroxytyrosol 4 mg/ml |
| G | Rosmarinic Acid 2.5 mg/ml | Aloin 1.5 mg/ml |
| H | Naringenin 1 mg/ml | Gallic Acid 1.5 mg/ml |
| I | Hesperetin 2 mg/ml | Gallic Acid 1.5 mg/ml |

In particular, in the method of the invention the step of contacting is performed for a period of time of less than 2 hours.

Preferably, the step of contacting is performed for a period of about one hour.

In a preferred embodiment of the invention, the contacting step is continued for a period of about 30 minutes.

In a more preferred embodiment, a first contacting step is repeated for one additional 30-minute period.

Optionally, between the two contacting steps, a rinsing step may be performed.

According to a preferred embodiment of the invention, the method is performed completely in the dark, i.e. avoiding any exposure to light.

As per the temperature of the contacting step, it is preferably performed at the temperature of about +35° C.±2° C.

In a preferred embodiment of the invention, after the contacting step, the matrix may be subjected to one or more washing steps.

Preferably, said washing step is performed with a suitable buffer; for example, a suitable buffer may be represented by phosphate buffer.

Each washing step may be performed for a period of about 15 minutes.

According to one embodiment of the invention, the method can be performed on both native biological matrix and biological matrix that had previously been treated for other purposes, for instance for stabilizing the protein, lipid and cell structures as well as lowering the potential antigenic action of the host.

For the purposes of the present invention, biological matrices may comprise: decellularized extracellular matrix, partially digested matrix and gelatins from animal origin.

For instance, before treating the biological matrix according to the method of the invention, it can be subjected to a treatment with glutaraldehyde, formaldehyde and quercetin.

According to an aspect of the invention, the method disclosed also inactivates xenoantigens in biological matrices.

With the term "xenoantigen" it is intended of animal origin that can be recognized by the immune system and can induce an antibody/immune-mediated/inflammatory response in the human host organism; in the present description the terms "xenoantigen", "antigen", "xenogeneic antigen", "epitope" and "crucial antigen" can have the same meaning, and can be used together or to substitute for each other.

For the purposes of the present invention, "xenoantigen" refers to the alpha-Gal epitope.

According to another aspect of the invention, the method disclosed prevents the thrombus formation and clots on and in a biological matrix.

According to a further aspect of the invention, the method disclosed prevents the lipid infiltration into a biological matrix.

According to a still further aspect of the invention, the method disclosed prevents the onset of an inflammatory process mediated by the cellular component.

According to another further aspect of the invention, the method disclosed prevents the formation of the microorganism biofilm on a biological matrix (biofouling).

In particular, the method of the invention has proved to prevent the formation of a biofilm formed by *Staphylococcus aureus* by decreasing the adhesive capacity on the prostheses surface.

The method of the invention is effective on both Gram⁻ and Gram⁺ bacteria.

A biological matrix obtained with the method of the invention is another object of the present application.

In particular, said biological matrix is represented by a cardiovascular bio-prostheses obtained with the method disclosed, which has a significant decrease in the formation of calcific deposits, structured thrombus, lipoproteins infiltration and significant resistance to bacterial adhesion and consequent tissue colonization.

According to a second object, the present invention discloses the biological matrix obtained with the method above described for use in the treatment of heart diseases in the medical or in the veterinary field.

As a further object of the present invention, it is disclosed a solution comprising a mixture of phenolic compounds to be used in the method of the present patent application.

In particular, said solution is prepared by mixing two or more phenolic compounds as above disclosed.

More in detail said solution might be prepared in a suitable buffer.

For example, a sodium phosphate buffer can be used.

Alternatively, the mixture of phenolic compounds may be prepared in a solution of NaOH.

The solution of the invention may be added with a suitable enzyme endowed with oxidase activity; for instance, there can be used tyrosinase, L-gulonolactone oxidase, laccase, etc.

The solution is preferably prepared in the dark, i.e. avoiding any exposure to light.

According to a third object of the invention, it is disclosed a kit for performing the above disclosed method.

In particular, said kit comprises:
a container containing a suitable buffer,
a container holding an adequate quantity of a mixture of phenolic compounds to be dissolved,
one or more containers holding the washing buffers;
an instruction booklet containing the description of the timings and modes of application of the procedure.

In an aspect of the invention, the phenolic compounds may be present in powder form to be dissolved in the buffer.

The present invention will be further described in connection with the following experimental section.

Experimental Section

In the following Experimental section, the term "knockout animal for the alpha-Gal antigen" refers to an animal in which the gene that encodes for the alpha-galactosyltransferase enzyme has been silenced. Such enzyme is responsible for attacking the membrane glycoproteins and lipoproteins of the alpha-Gal epitope. Its absence causes the production of tissues that lack the epitope in question entirely and which in this respect are entirely comparable to the tissue of the human body. In the present invention, knockout animal vascular tissues for the alpha-Gal antigen were used as absolute negative control.

Xenoantigen Inactivation

Commercial Trifecta GT™ bioprosthetic aortic heart valves were extracted from their packaging and subjected to two washing steps in phosphate buffer for 15 minutes each. Different solutions were prepared based on the phenolic mixtures reported above and filtered with a 0.2 μm sterile membrane. The Trifecta GT™ valves were incubated with each single solution under moderate but constant stirring in the dark, for two step of 25±5 minutes each, at room temperature.

At the end of the incubation, the treated bioprosthetic heart valves were washed twice in phosphate buffer for 15 minutes each.

A set of original Trifecta GT™ valves were adopted untreated off-the-shelves as control.

The assessment of the presence of any epitopes still active on the surface of the treated samples is based on a modification of the illustrated method by the inventors and described in the Italian patent no. 0001409783 and in EP 2.626.701.

Briefly, tissue samples from the treated and untreated Trifecta™ valves were placed in test tubes to which a phosphate buffer is added up to a final volume comprised between 1000 μL and 1500 μL.

Then, a monoclonal mouse antibody, directed against the alpha-Gal epitope, is added (in the present example this is an IgM clone called M86), at the preferable concentration of [1:50] v/v and the whole is incubated for 120±10 minutes at 37±2° C. under constant but moderate stirring.

At the end, the samples were subjected to centrifugation at 14,750×g for 30±5 minutes at ambient temperature.

During the incubation with the M86 antibody, a 96-well plate was prepared, in which the bottom of the wells is lined with 100 μL per cell of alpha-Gal/serum albumin at 5 μg/ml in phosphate buffer. The plate thus prepared was incubated for 60±10 minutes at a temperature comprised between 30° C. and 40° C., although it is preferable to stabilize everything at 37° C.

Then 3 washes were performed with 300 μL per well with a phosphate buffer at ambient temperature. The first washing was left to act for 5 minutes, and the two subsequent washes for 3 minutes.

The blocking was done with 300 μL per well with serum albumin, followed by incubation for 60±10 minutes at ambient temperature, in darkness. Subsequently, 3 washes as above were performed.

For each well, 100 μL of supernatant, taken after centrifugation from each treated sample, was added.

The samples were loaded into the plate, each type of sample occupying the wells of an entire column. There follows incubation of the plate for 120±10 minutes at a temperature comprised between 30° C. and 40° C., although it is preferable to stabilize everything at 37° C.

Then 3 washes as above were performed, and 100 μL per well is added of a solution of secondary antibody (rabbit polyclonal anti-mouse) conjugated with peroxidase enzyme (the ideal solutions of such antibody have been found to be [1:1000], [1:500] and [1:100], preferably the intermediate one [1:500] was adopted).

The plate is then incubated again for 60±10 minutes at a temperature comprised between 30° C. and 40° C., although it is preferable to stabilize everything at 37° C.

Then 3 washes as above were performed. 100 μL is added per well of a development solution for the peroxidase enzyme, followed by incubation of the plate for 5±1 minute in darkness.

Subsequently, 50 μL was added per well of a stop solution constituted by $H_2SO_4$ 2M, and the plate is then read in a plate reader at 450 nm.

An overall analysis of the various adopted polyphenol mixtures shows that it is possible to obtain an inactivation of the alpha-Gal antigen in the treated Trifecta™ valves between 80±2% and 95±0.8% compared to the untreated samples.

The same type of valve, treated and non-treated has been subjected to the following in-vitro and in-vivo analysis.

In particular, the treatment has been performed with a solution according to the present invention.

Evaluation of FACTA™ Treatment Stability in Time

The FACTA™ treatment is based on the action of a mixture containing specific polyphenols according to the present invention. However, polyphenols at certain dosages can be toxic (LD50 5 g/Kg), accumulating in the liver and kidneys. To confirm the stability of the FACTA™ treatment, we evaluated the release of phenolic residues over time. After FACTA™ treatment, commercial BHVs leaflets were left in the storage solution as supplied by the manufacturer. At different time-point of 7 and 14 days and 1, 3 and 9 months, the amount of phenolic compounds released from the tissue was determined (n=9 samples for each time point). As a control, a set of untreated commercial BHV leaflets were analyzed at same time-point. The total polyphenol content present in the solutions was evaluated using a protocol based on the reaction, under conditions of alkaline pH, between the phenolic compounds eventually present in the storage solution and diazonium salts. The reaction product is a stable chromophore that can be detected and quantified by absorbance analysis at a wavelength of 480 nm. The concentration of phenols present in the sample is quantified by an external calibration method with a catechin standard and is therefore expressed as a millimolar concentration of catechin equivalent (mM).

The results are shown in FIG. 1.

Totally, 160 ppm of phenolic compounds were released from a treated tissue in 9 months. The release occurs almost in the first 14 days after the treatment. Concerning the toxic potential, it can be confirmed that the total amount of polyphenols leakage from the treated tissues does not result in any health risk; in fact, it is lower than the concentration of polyphenols present in the human plasma following the uptake with the diet.

In-Vitro Calcification Assay

Leaflets from untreated (B) and FACTA™ treated (BT) commercial BHVs, native (WT) and FACTA™ treated native aortic porcine leaflets (WT T) and alpha-Gal knockout porcine aortic leaflets (KO) were incubated in pooled normal human serum (Innovative Research, Peary Court Novi, MI) with 2% of penicillin and streptomycin for 14 days at 37° C. As a control, a set of samples was incubated in PBS in the same condition. After incubation, samples were washed twice in PBS for 10 min and subjected to acid hydrolysis in $HNO_3$ at 110° C. for 12 h. Calcium evaluation was performed in hydrolyzed samples by inductively coupled plasma according to the directives of the EPA6010D method and expressed as μg $Ca^{2+}$/mg of dry defatted weight (d.d.w.).

Figure 2:
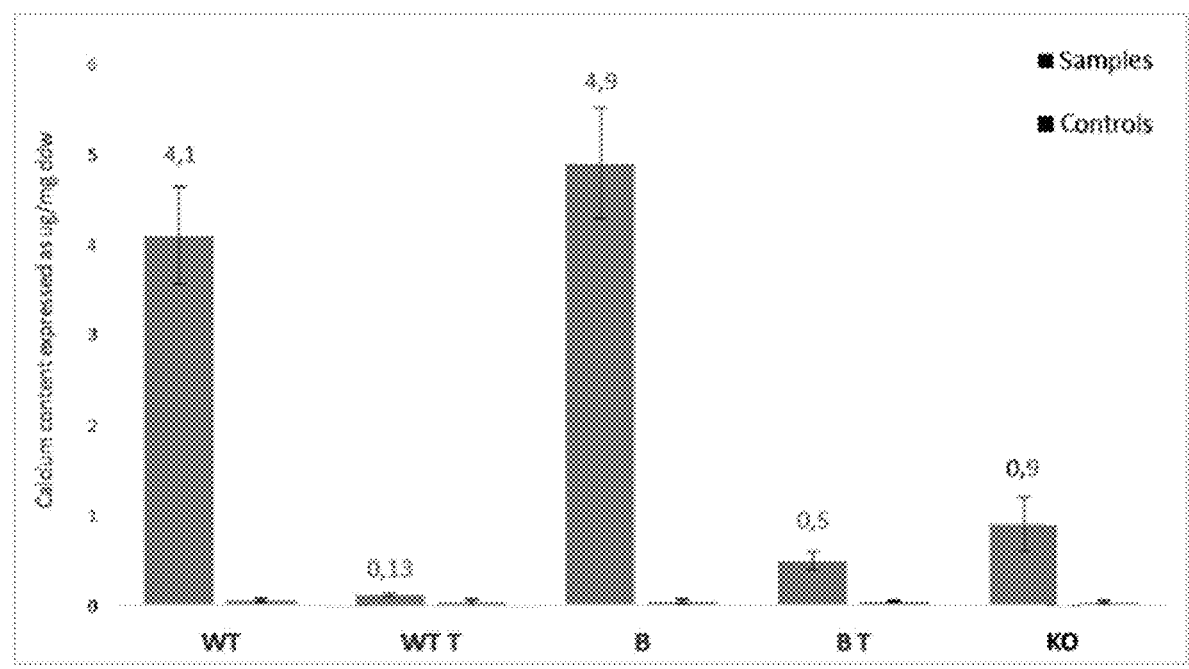
FIG. 2: results of the in-vitro calcification assays.

The results are reported in FIG. 2.

FACTA™ treated BHV (BT) shows a decrease in the calcific propensity of 90% (B vs BT $p<0.05$) and of 44.4% (BT vs KO, $p<0.05$) when compared with untreated BHVs (B) and alpha-Gal knockout tissues (KO) respectively. Knockout tissue is considered the least calcifying biological support and is used as an absolute negative control in xenotransplant-induced calcification studies. FACTA™ treated BHV has been shown to calcify almost 50% less than the KO standard. If the FACTA™ method is applied to a native tissue (WT T, not fixed with glutaraldehyde), the anti-calcifying effectiveness compared to the reference tissue KO rise to 85% (WT T vs KO $p<0.05$).

Hydrodynamic Assessment

Figure 3:
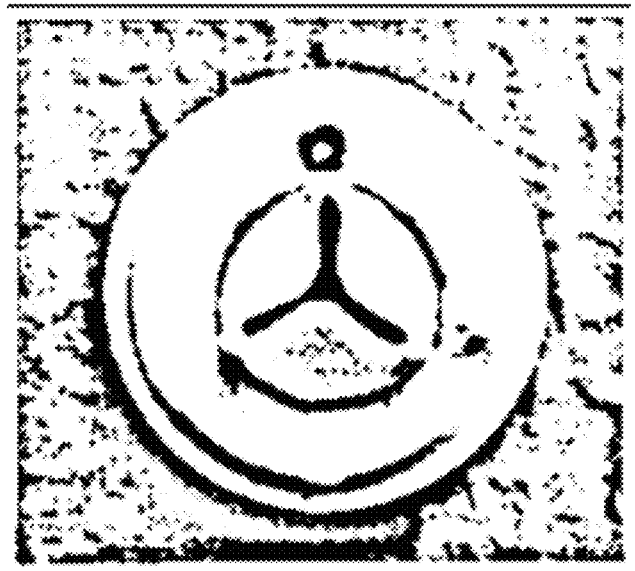
FIG. 3: the valve placed in the custom-fabricated silicone holder.

The hydrodynamic performance of the valves was assessed under simulated pulsatile flow in a Vivitro® Pulse Duplicator System (Vivitro Labs Inc., Victoria, BC, Canada). The flow simulator was used to model the left side of the heart. The test valves were fitted into a custom-fabricated silicon holder (FIG. 3) and placed in the aortic position of the pulsatile flow system. A 25 mm Bjork-Shiley tilting disc valve was used in the mitral position as a reference valve. The testing was performed in 0.9% (w/v) NaCl at room temperature. The valves were tested under five pulsatile flow conditions (Table 1), according to ISO 5840-3. The flow conditions corresponded to cardiac outputs between 2.5-9 l/min. During testing, the diastolic/systolic pressure was set to 80/120 mm Hg, whereas the systolic duration occupied 35% of the cardiac cycle. At each flow condition the valves were preconditioned for 5 min, before the pressure and flow signals were recorded over 10 cycles at each flow condition for each valve group (FACTA™ treated BHVs, n=3; untreated BHVs, n=2).

TABLE 1

Pulsatile flow conditions used in the hydrodynamic assessment.

| Flow condition | Cycle rate (bpm) | Stroke volume (ml) |
|---|---|---|
| 60/60 | 60 | 60 |
| 72/70 | 72 | 70 |
| 80/70 | 80 | 70 |
| 100/80 | 100 | 80 |
| 120/80 | 120 | 80 |

The hydrodynamic performance of the valves was assessed in terms of the mean pressure drop (MPD) and peak pressure drop (PPD) across the valve, root mean square forward flow through the valve ($Q_{RMS}$), peak forward flow through the valve (QPEAK), valve effective orifice area (EOA), reverse flow through the valve during valve closure and while the valve was fully closed, and valve energy losses. As defined in ISO 5840-3, the EOA was measured using only the volumetric flow rate and the pressure difference across the valve during the positive pressure interval of the forward flow phase. The results for each test were averaged over the number of cycles recorded (n=10). The data was analyzed in Microsoft Excel® and Prism® 7 for Windows (v7.03, GraphPad Software Inc., California) and expressed as mean±standard deviation (SD). Two-sided unpaired I-test was used to assess significant differences between the treated and untreated groups, at the 0.05 confidence levels.

Figure 4:
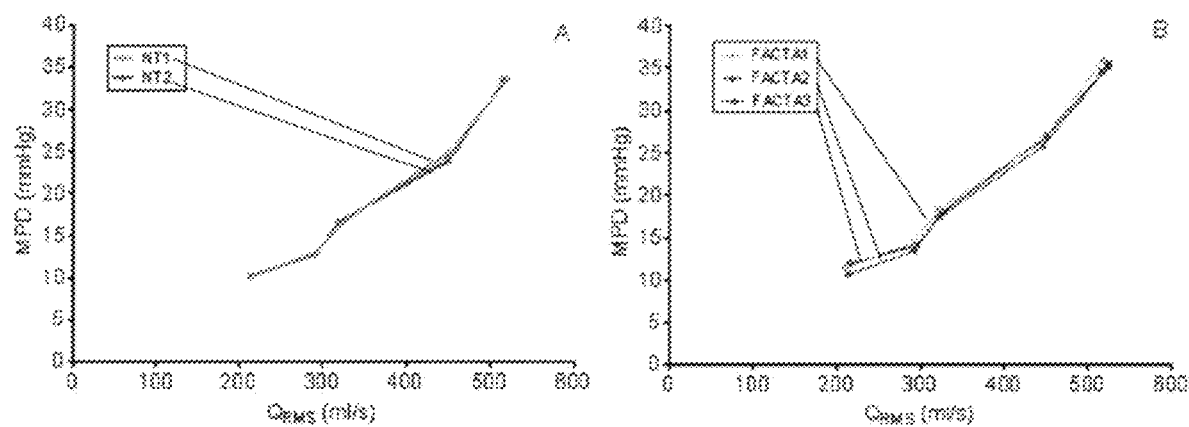
FIG. 4: MPD-$Q_{RMS}$ profiles of the untreated (A) and FACTA™ treated (B) commercials BHVs; the data represents means±SD (number of cardiac cycles averaged, n=10).

The MPD-$Q_{RMS}$ profiles of the untreated and treated valves, averaged over 10 cycles at each flow condition, are illustrated in FIGS. 4A and 4B, respectively. Both valve groups demonstrated excellent repeatability and similar $Q_{RMS}$-PD profiles between them.

Figure 5:
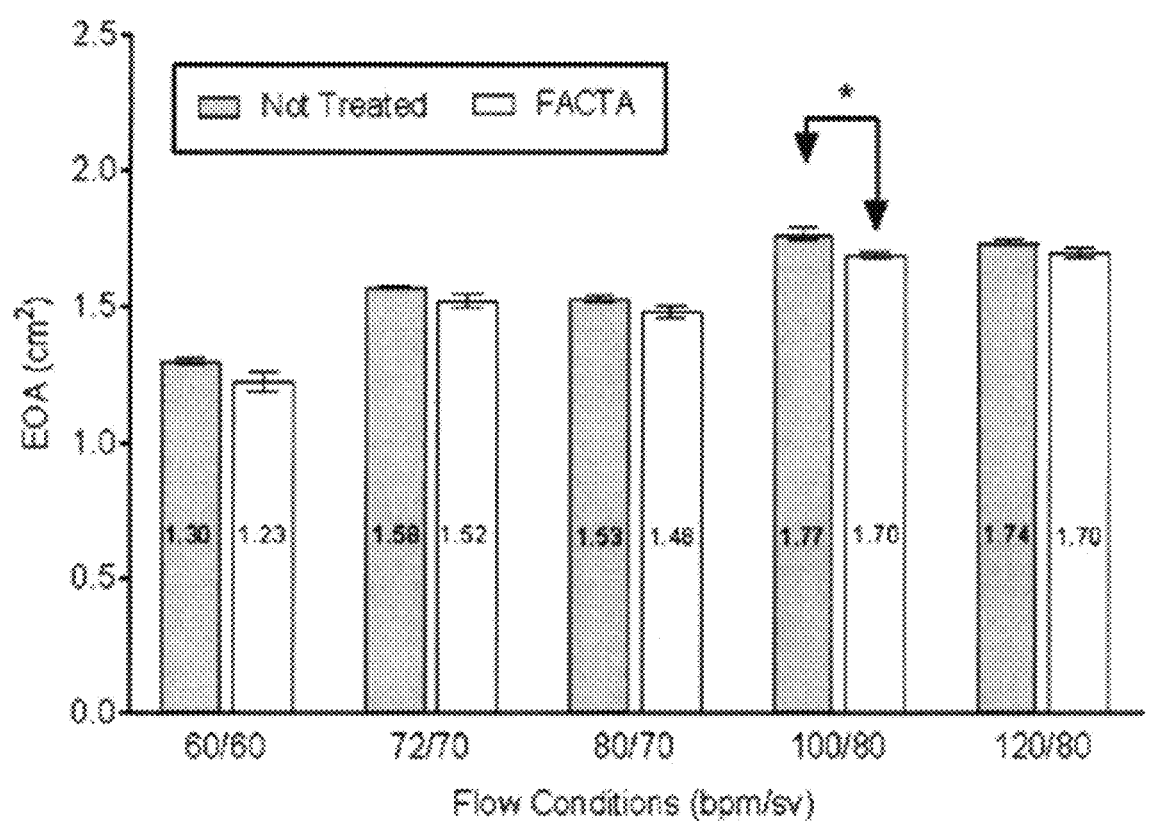
FIG. 5: mean EOA of the untreated (n=2) and FACTA™ treated (n=3) valve groups at each flow conditions tested; data represents means±SD. Asterisks indicate significance differences between treated and untreated group.

The mean EOAs of the treated and untreated valves calculated for each flow condition is illustrated in FIG. 5. There was no statistically significant difference in EOA between the untreated and treated group, apart from flow condition 100/80 (bpm/sv), at which the treated group demonstrated a significantly smaller (p<0.05) EOA compared to the untreated one.

Figure 6:
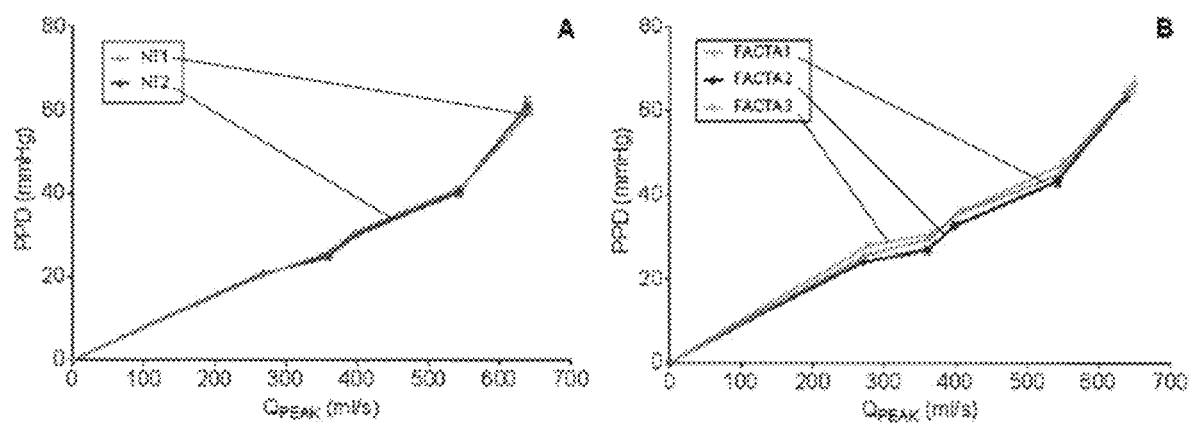
FIG. 6: PPD-QPEAK profiles of the untreated (A) and FACTA™ treated (B) commercial BHVs. Data represents means±SD (number of cardiac cycles averaged, n=10).

The PPD-$Q_{PEAK}$ profiles of the untreated and treated valves, averaged over 10 cycles at each condition, are illustrated in FIGS. 6A and 6B, respectively. Both groups demonstrated similar PPD-$Q_{PEAK}$ profiles.

Figure 7:
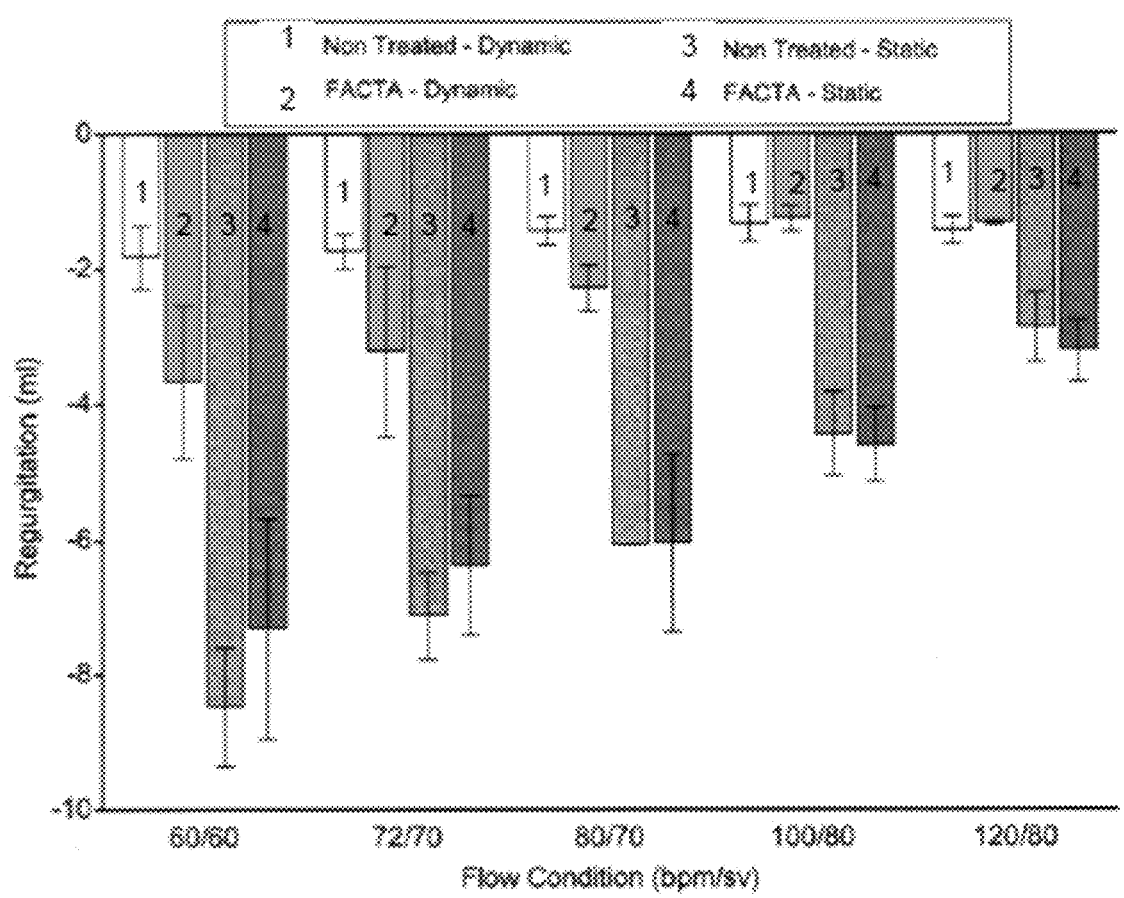
FIG. 7: mean regurgitation of the untreated (n=2) and FACTA™ treated (n=3) valve groups at each flow conditions tested (means±SD).

The mean dynamic and static regurgitation volumes of the untreated and treated groups at each flow conditions are illustrated in FIG. 7. The dynamic regurgitation (closing volume) and static regurgitation (closed volume) for both groups were negative representing back-flow through the valves. In general, the regurgitation volumes were more significant for the lower flow conditions and increased with increasing flow rates. No statistically significant differences were found in the regurgitation volumes between the untreated and treated groups.

Figure 8:
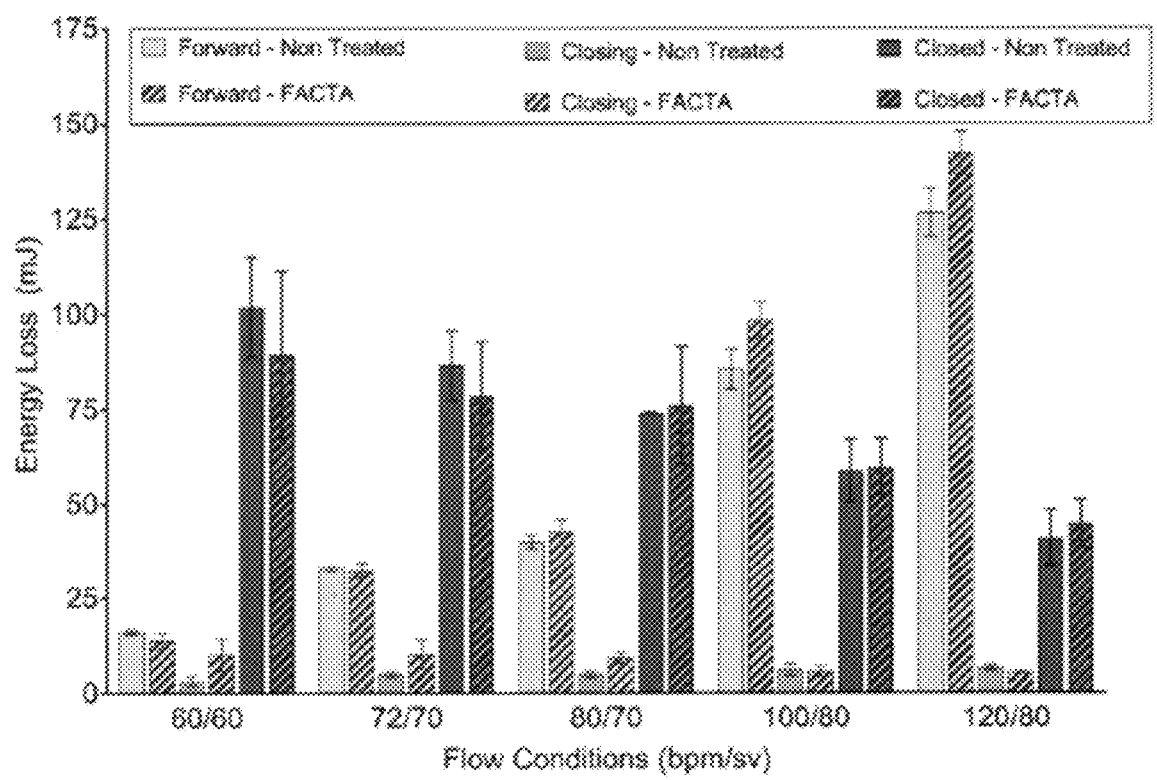
FIG. 8: mean energy losses for the untreated (n=2) and FACTA™ treated (n=3) valve groups at each flow conditions tested (mean±SD).

The mean energy losses for the treated and untreated groups are illustrated in FIG. 8. With increasing flow condition, an opposite pattern was observed for the energy losses in the forward flow and closed phase. The lowest energy loss during the forward flow phase was observed for the low-flow condition (60/60) and, increased with increasing flow rates. In contrast, the highest energy loss during the closed phase was observed for the low-flow condition and decreased with increasing flow rates. There was no significant difference in the energy losses between the untreated and treated groups, in any of the flow conditions tested.

Biomechanical Assessment

Low-strain rate uniaxial tensile loading to failure was carried in a Instron® tensile tester (5967 Dual Column Series) with a 100 N load cell. One leaflet was excised from each valve and used to isolate a specimen with test dimensions 6×3 mm (length×width). The thickness of the samples was measured at 3 points along their length, using a Mitutoyo® thickness gauge and averaged. During testing, each sample was preloaded to 0.01 N, at a strain rate of 20 mm/min, and then loaded to failure at the same rate. The recorded load-extension response of each sample was converted to engineering stress-engineering strain. The stress-strain curves were used to calculate the elastic and collagen phase slopes, transition stress and strain, failure strain and ultimate tensile strength. The data was analysed in Excel and expressed as mean±SD. Two-sided unpaired t-test was used to assess significant differences between the treated and untreated groups at the 0.05 confidence level.

Figure 9:
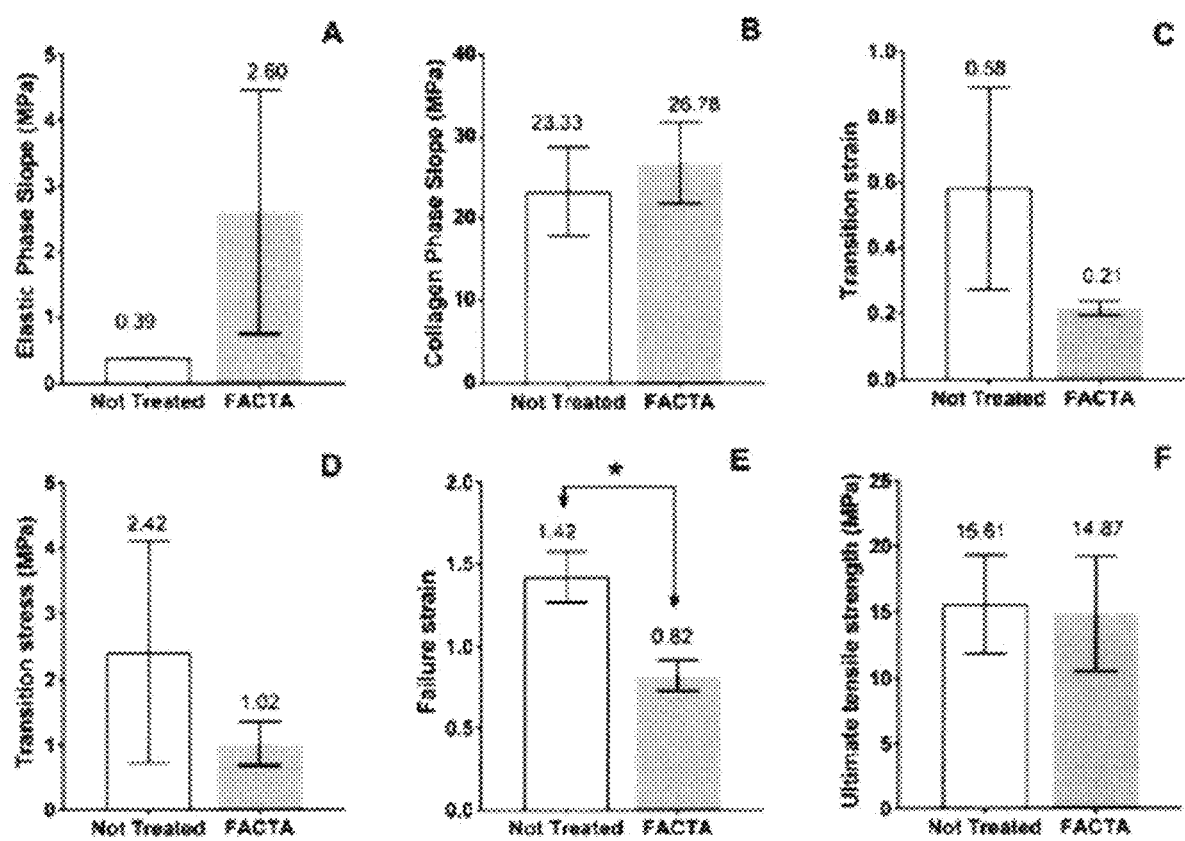
FIG. 9: mean biomechanical parameters for the untreated (n=2) and FACTA™ treated (n=3) valve groups (means±SD). A: Elastic phase slope; B: collagen Phase slope; C: Transition strain; D: Transition stress; E: Failure strain; F: Ultimate tensile strength. Asterisks indicate a significant difference between the untreated and treated groups for the specific parameter indicated.

The mean biomechanical parameters of the FACTA™ treated and untreated groups are shown in FIG. 9. Significant differences between the treated and untreated groups were found in the case of the failure strain (p<0.05). No significant differences were found in any of the other parameters between the FACTA™ treated and untreated groups. Although no statistical significance was found in the case of the elastic phase slope (FIG. 9A) and transition strain (FIG. 9C) between the two groups, these parameters were shown to be increased (elastin phase slope) or decreased (transition strain) for the treated group compared to the untreated one. A higher elastic phase and a lower transition strain would indicate a stiffer and less extensible material, respectively, under low strain.

In-Vivo Investigation on Swine Animal Model

Figure 10:
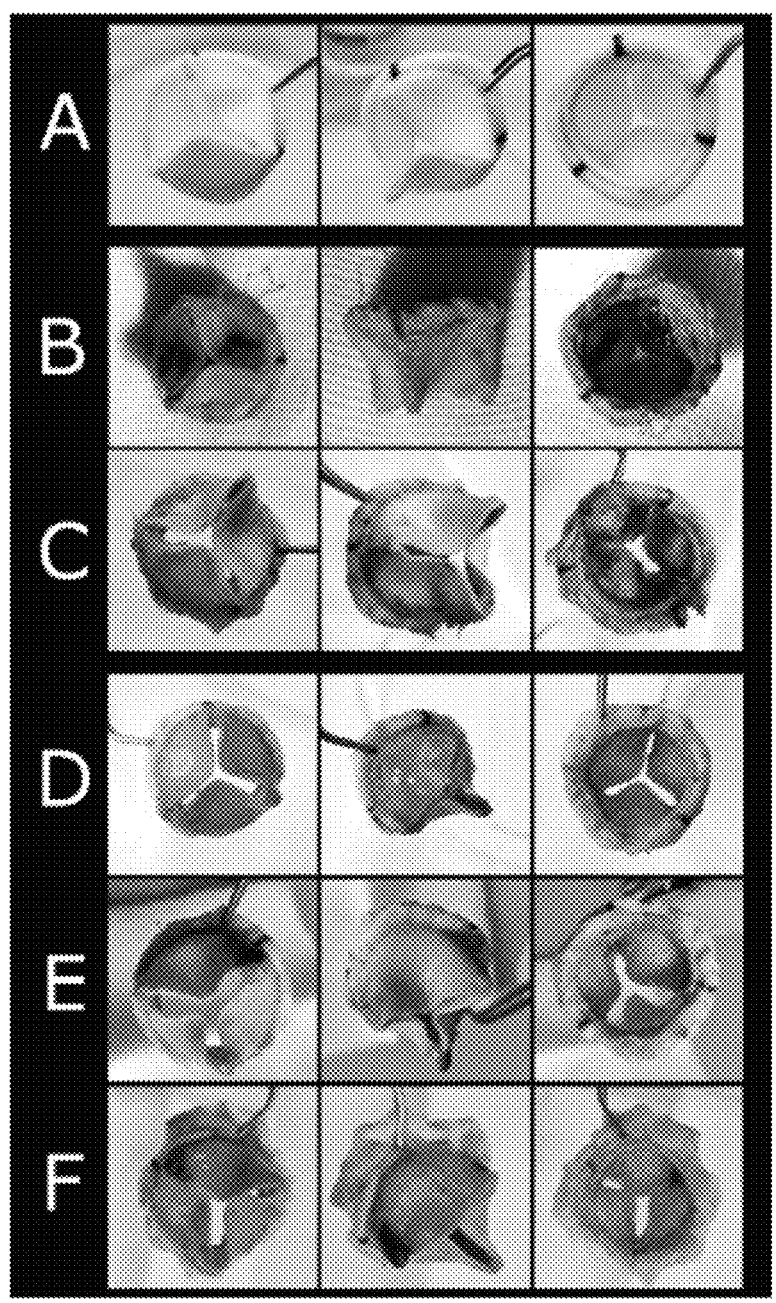
FIG. 10: some of the most significant commercial BHVs explanted from swine after 1 month of follow-up. FACTA™ treated BHVs (D, E, and F), untreated BHVs (B and C), non-implanted BHV (A).

FACTA™ treated (n=5) and untreated (n=3) commercial Trifecta GT BHVs (St. Jude Medical, USA) were implanted in pulmonary position in a pig animal model. After 1 month of follow-up, the BHVs were removed for investigation. Explanted BHVs were washed with two 15-minute steps in sterile PBS at 4° C. and immediately photographed for macroscopic evaluation (FIG. 10). Subsequently, the leaflets were individually excised from each valve. The cusps for the histological and immune-histochemical investigations were immediately included in OCT (Optimal Cutting Temperature) compound and the remaining leaflets were subjected to alpha-Gal quantification by ELISA test. A non-implanted Trifecta BHV was used as a referred control.

Macroscopic Visual Examination

Figure 11:
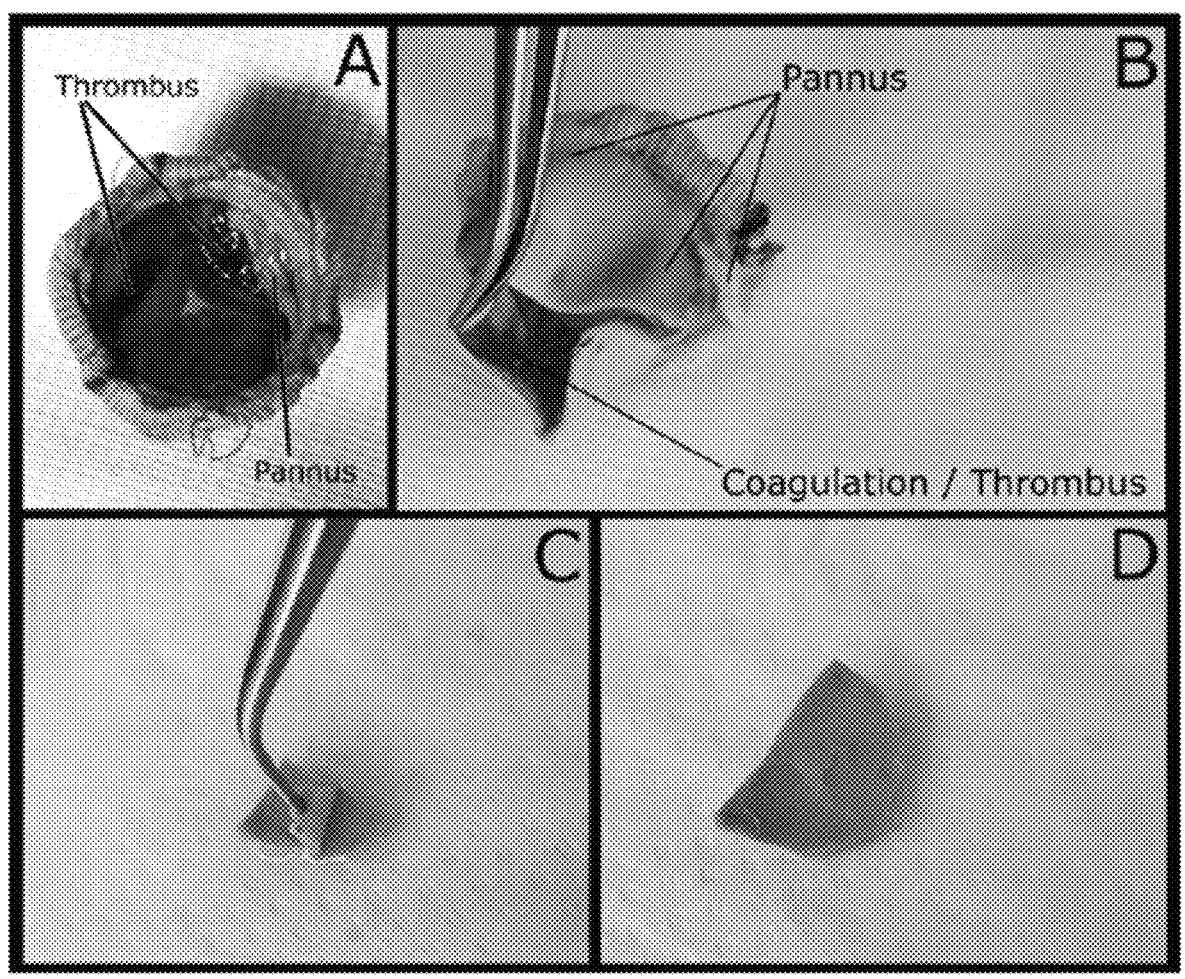
FIG. 11: macroscopic aspects of untreated commercial BHVs after 1 month of follow-up in a common swine model. It is evident the formation of blood clots (A) and of a fibrotic pannus affecting the cusps (A, C and D) and the suture ring of the prostheses (B).

As can be seen from FIG. 10, the untreated commercial BHVs, compared to the FACTA™ treated ones, show the presence of a critical fibrous deposit and blood clots on the ventricular surface. These peculiar characteristics of untreated BHVs, together with the formation of a homogeneous and thick pannus both around the suture ring and on the aortic surface of the cusps are better detectable on FIG. 11.

Histological Analysis

Tissues were embedded in OCT compound (Tissue Tek; Sakura Finetek, Tokyo, Japan), cryo-cooled in liquid nitrogen, and cut into 6-mm cryo-sections. Histological analyses were performed by the use of commercial kit from Bio-Optica (Milan, Italy) according to the indications provided by the manufacturer. The histo-kits used are listed in Table 2.

TABLE 2

Histological kits used and their experimental significance.

| Histological Kit | Detected components - Meaning |
|---|---|
| Hematoxylin & Eosin | Assessment of the general aspect of the connective tissue/ detection of cellular component |
| Von Kossa | Evaluation of the presence of calcific deposits |
| Picro Mallory Trichromic | Assessment of the general aspect of the connective tissue, particularly referred to collagen and elastin components. Evaluation of the presence of fibrin deposition and structured thrombus. |
| Oil Red O | Assessment of the presence of lipid infiltrates |

Figure 12:
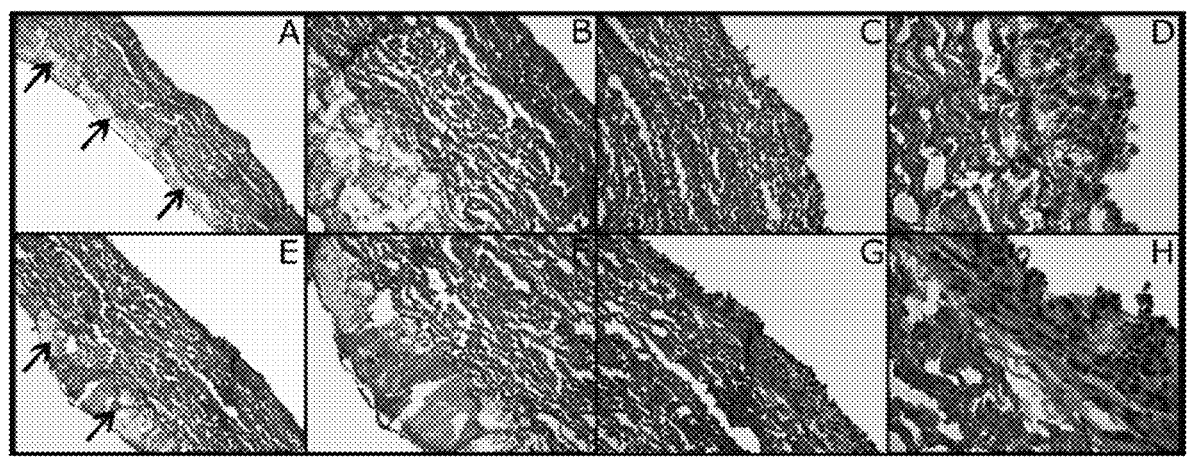
FIG. 12: Hematoxylin & Eosin staining of untreated commercial BHVs after 1 month of follow-up in swine. The black arrows (box A and E) highlight the presence of a dense and homogeneous fibrotic layer on and in the ventricular surface of the leaflets. A foreign body reaction is present in the other side of the leaflets (box C and G) with inflammatory cells penetration (box D and H). Box A and E magnification 4×. Box B, C F and G magnification 10×. Box D and H magnification 40×.
Figure 13:
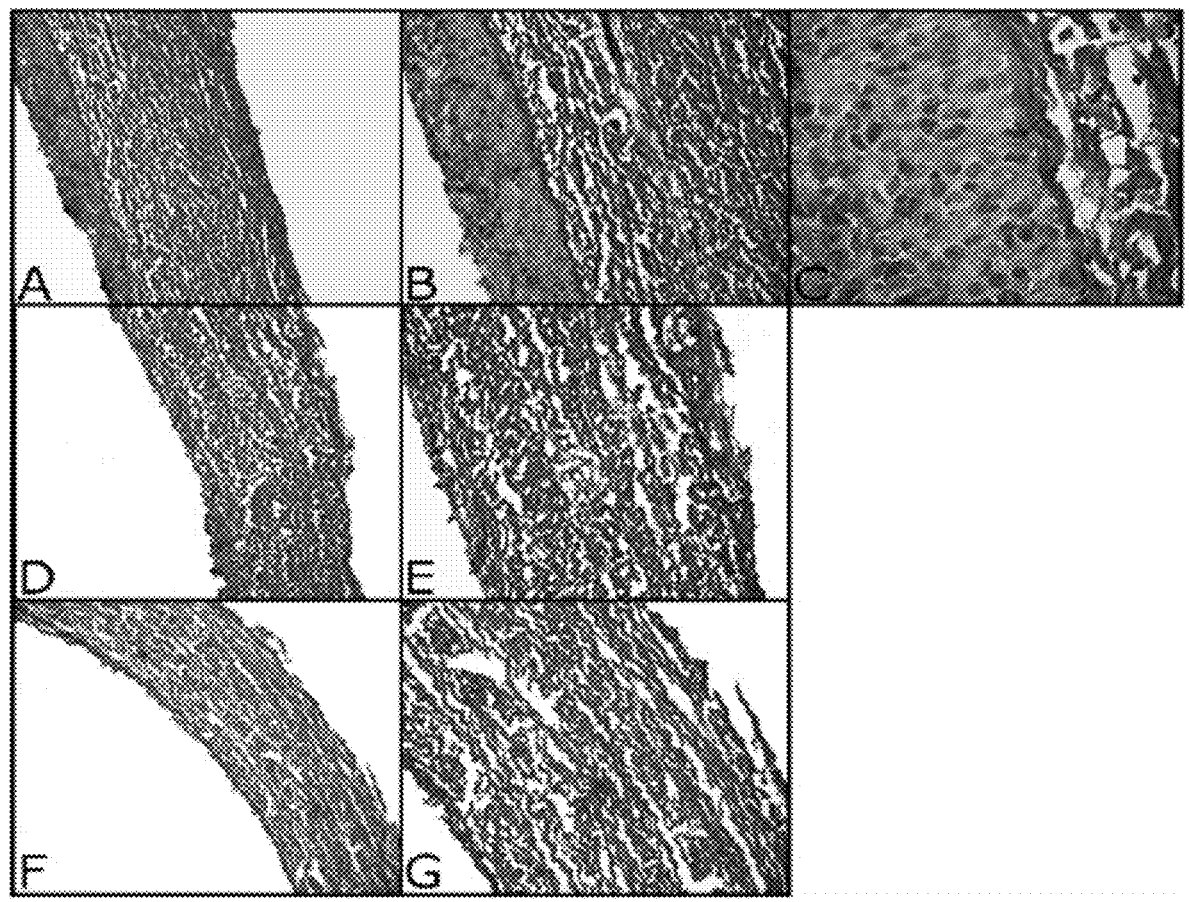
FIG. 13: Hematoxylin & Eosin staining of FACTA™ treated commercial BHVs after 1 month follow-up in the swine. Where foreign body reaction occurs (box A), no cellular penetration is appreciable (box C). Box A, D and F magnification 4×. Box B, E and G magnification 10×. Box C magnification 40×.

Generally, leaflets from untreated valves report the presence of a homogeneous fibrotic pannus on the ventricular surface as highlighted by the black arrows in FIG. 12 (Box A and E). A foreign body reaction is clearly visible in all the explanted cusps, both untreated (FIG. 12) and FACTA™ treated commercial BHVs (FIG. 13). It should be noted that in untreated commercial valves the cellular component is able to penetrate the matrix (FIG. 12 box D and H).

The FACTA™ treatment seems to be able to exert a barrier effect that counteracts the penetration into the inner stroma of the inflammatory cellular component (FIG. 13, box C) responsible for the subsequent degeneration of the extracellular matrix.

Figure 14:
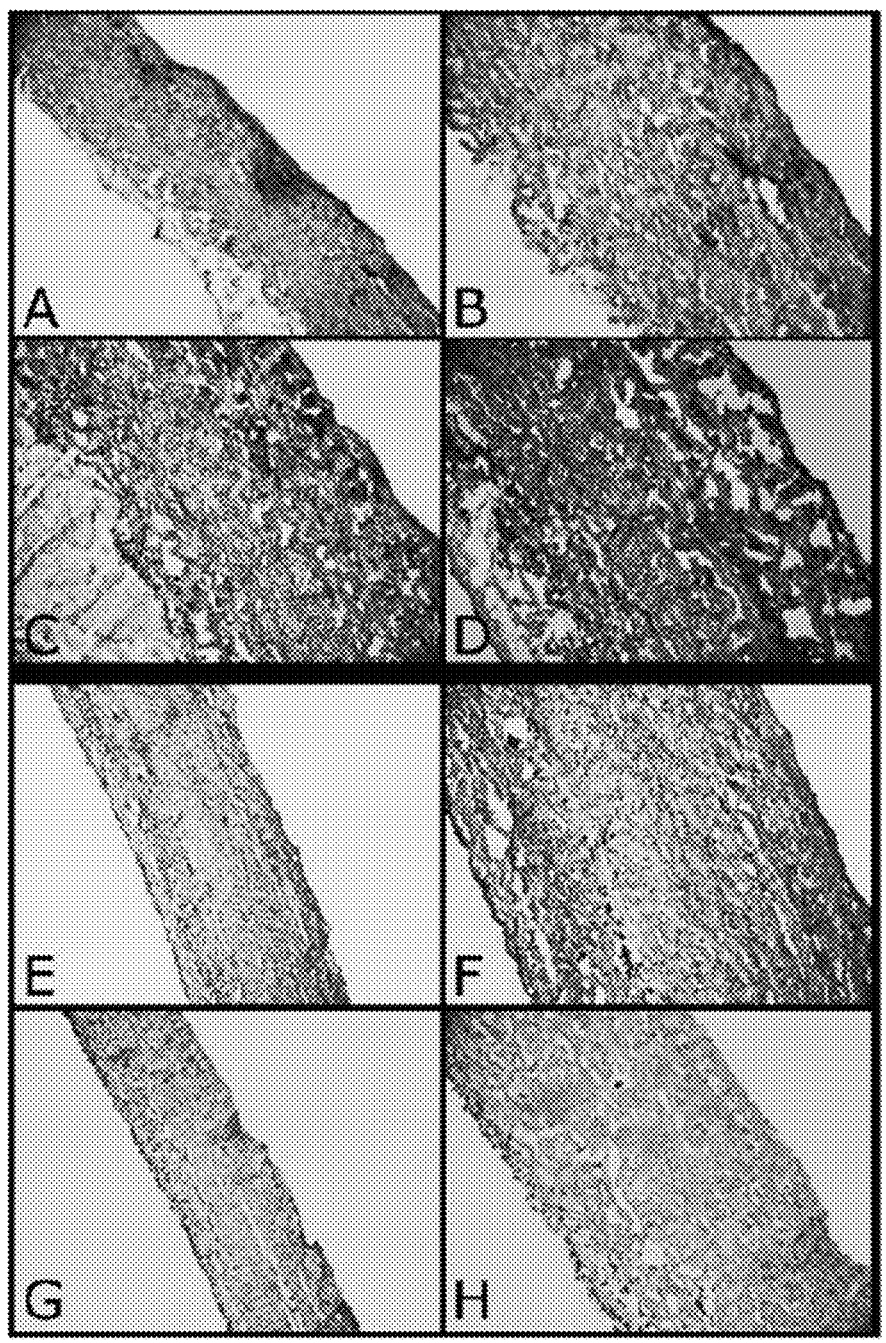
FIG. 14: Oil Red "O" staining for lipid identification. FACTA™ treated (E, F, G and H) and untreated (A, B, C and D) commercial BHVs after 1 month of follow-up in the swine. Red colour reveals the presence of lipid infiltration. Box A, C, E and G magnification 4×. Box B, D, F and H magnification 10×.

In the untreated valves, in the area subtended to the fibrous pannus and adjacent to the cellular layer it is possible to observe the presence of a rich lipid infiltrate, as reported in FIG. 14 (box A, B, C and D), probably due to the action of monocytes incapable of processing LDL. The monocytes incorporate the lipid drops, but not being able to degrade them, become foam cells subsequently working as enucleation site for calcium deposition. The FACTA™ treatment guarantees preservation of the tissue from this critical condition (FIG. 14, box E, F, G and H, no lipid infiltration are present).

Figure 15:
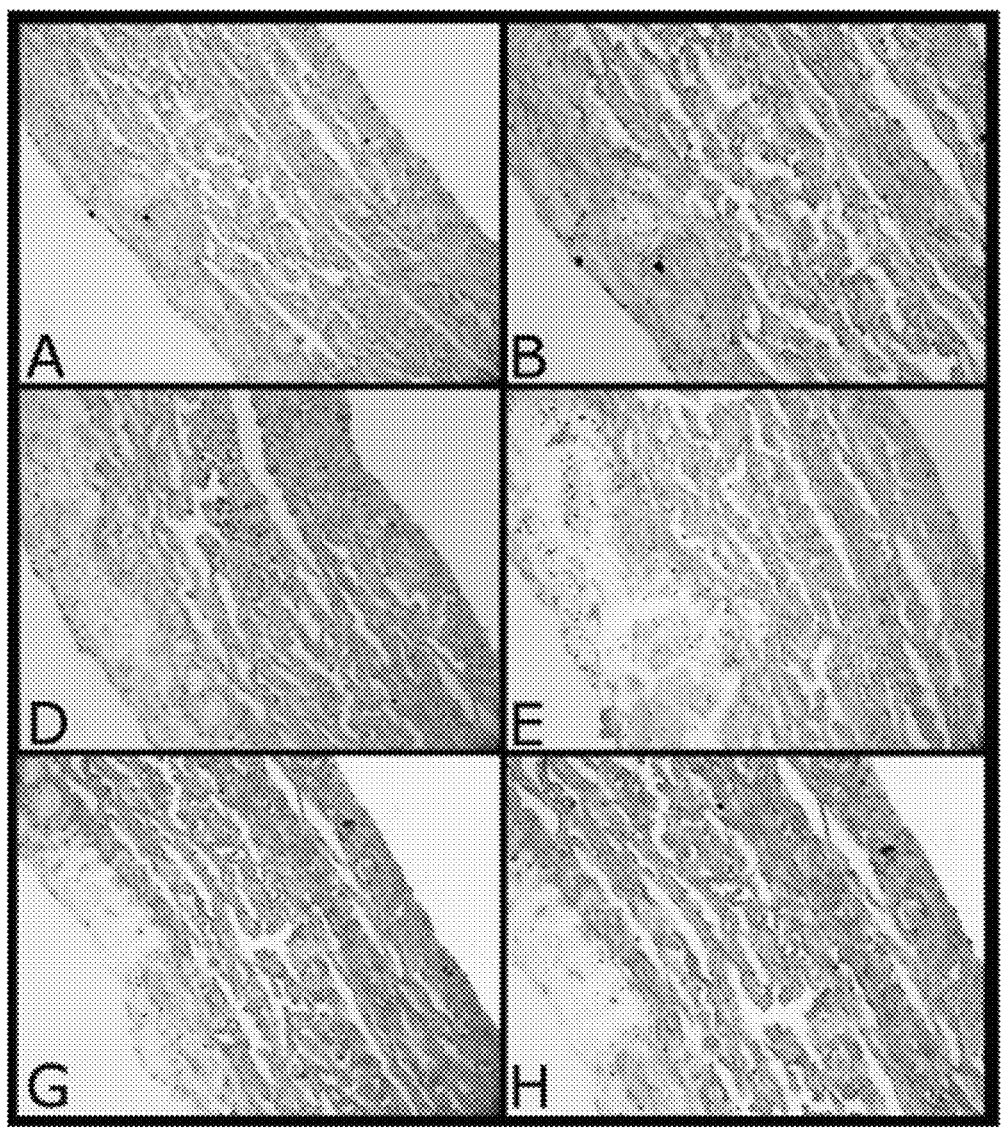
FIG. 15: Von Kossa staining of untreated commercial BHVs after 1 month follow-up in the swine. Evident calcium deposition, especially at the level of the external interfaces of the leaflets, were reported. Wide spreads of microcalcifications affecting the internal portion of the stroma are visible. Box A, D and G magnification 4×. Box B, E and H magnification 10×.

As predictable from the massive presence of lipid infiltrates, the untreated commercial BHVs after 1 month of follow up in swine are markedly calcified, with evident calcium accumulations especially at the level of the external interfaces of the leaflets (FIG. 15). Where large deposits of calcium are not evident, however, wide spreads of micro-calcifications affecting the internal portion of the stroma are reported (FIG. 15, box D, E, G and H).

Figure 16:
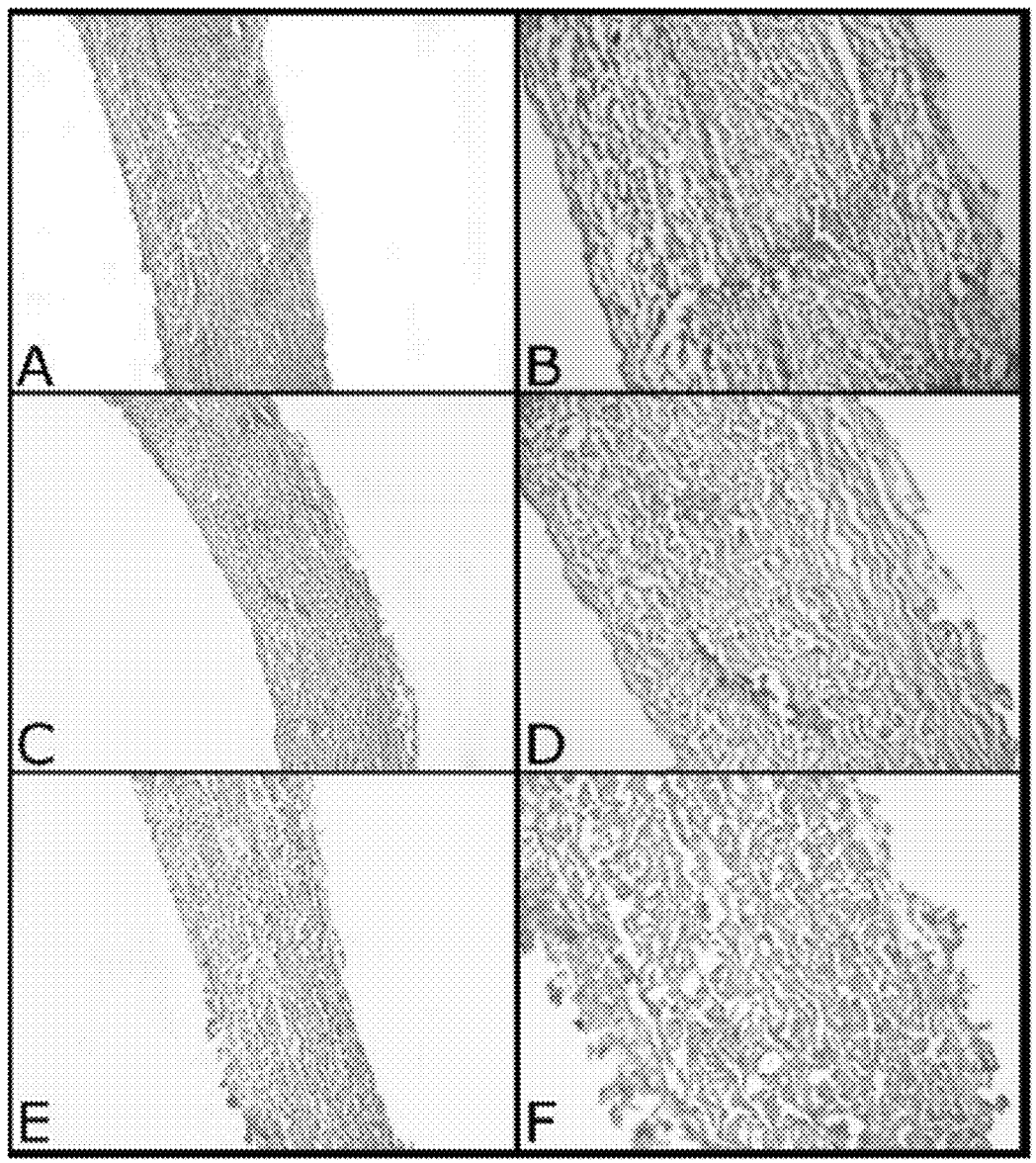
FIG. 16: Von Kossa staining of FACTA™ treated commercial BHVs after 1 month follow-up in the swine. No calcium deposit was observable. Complete absence of micro-calcification. Box A, C and E magnification 4×. Box B, D and F magnification 10×.

The FACTA™ treated commercial BHVs are optimally preserved from calcium deposition, as can be seen in FIG. 16.

Figure 17:
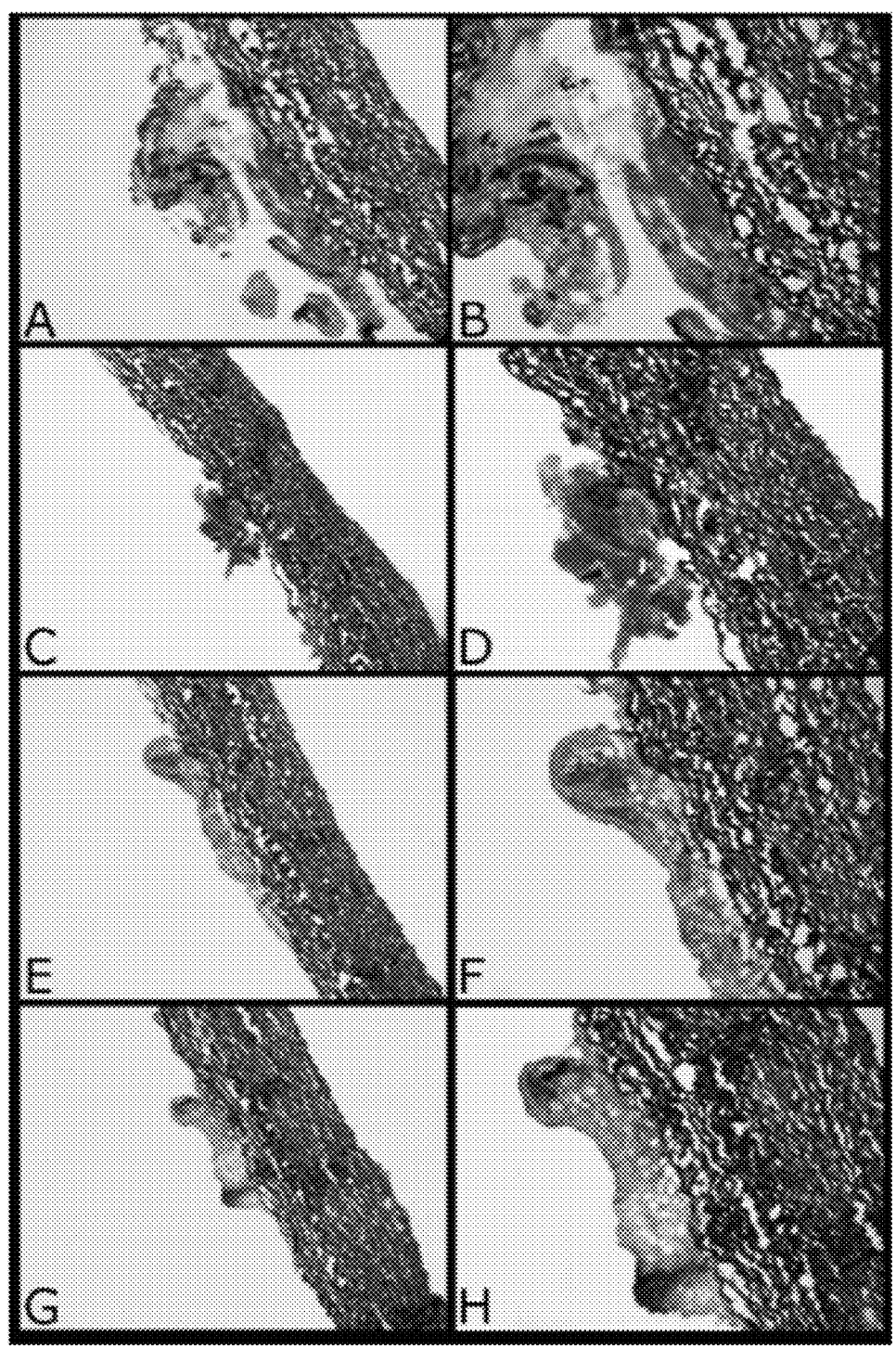
FIG. 17: Mallory Trichromic staining of untreated commercial BHVs after 1 month follow-up in the swine. The collagenic matrix is recognizable in blue colour, the presence of structured thrombi in red/yellow. Box A, C, E and G magnification 4×. Box B, D, F and H magnification 10×.

In addition to the development of fibrous pannus, the untreated commercial valves showed a very strong propensity for the development of structured thrombi on the ventricular surface of the leaflets, as shown in FIG. 17.

Figure 18:
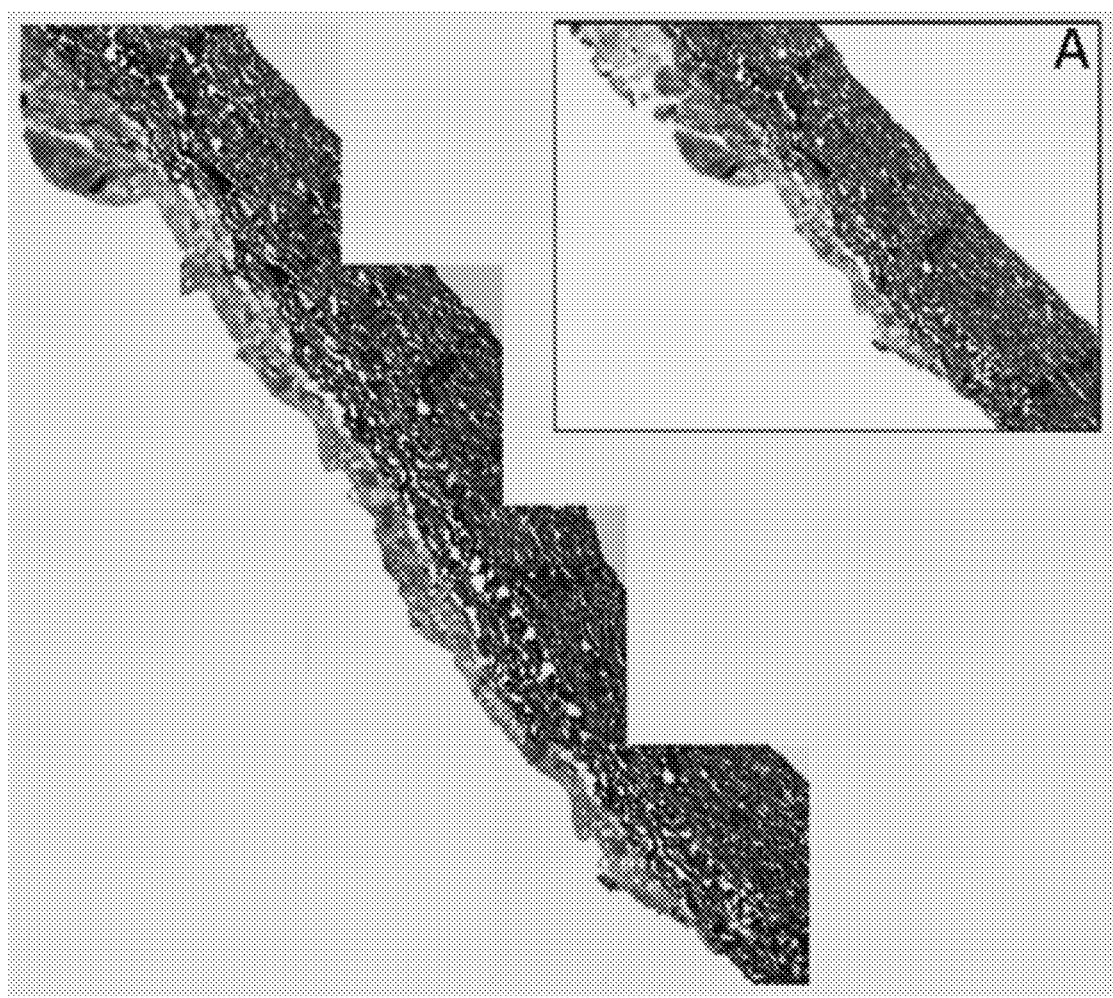
FIG. 18: Mallory Trichromic staining of untreated commercial BHVs after 1 month of follow-up in the swine. In red/yellow colour is clearly evident the presence of a fibrous pannus that culminates in a thrombus in the ventricular surface of the leaflet. Box A, magnification 4×, multiple panel magnification 10×.

In particular, in FIG. 18 is reported a panel showing the presence of a fibrous pannus that culminates in a structured thrombus formation.

Figure 19:
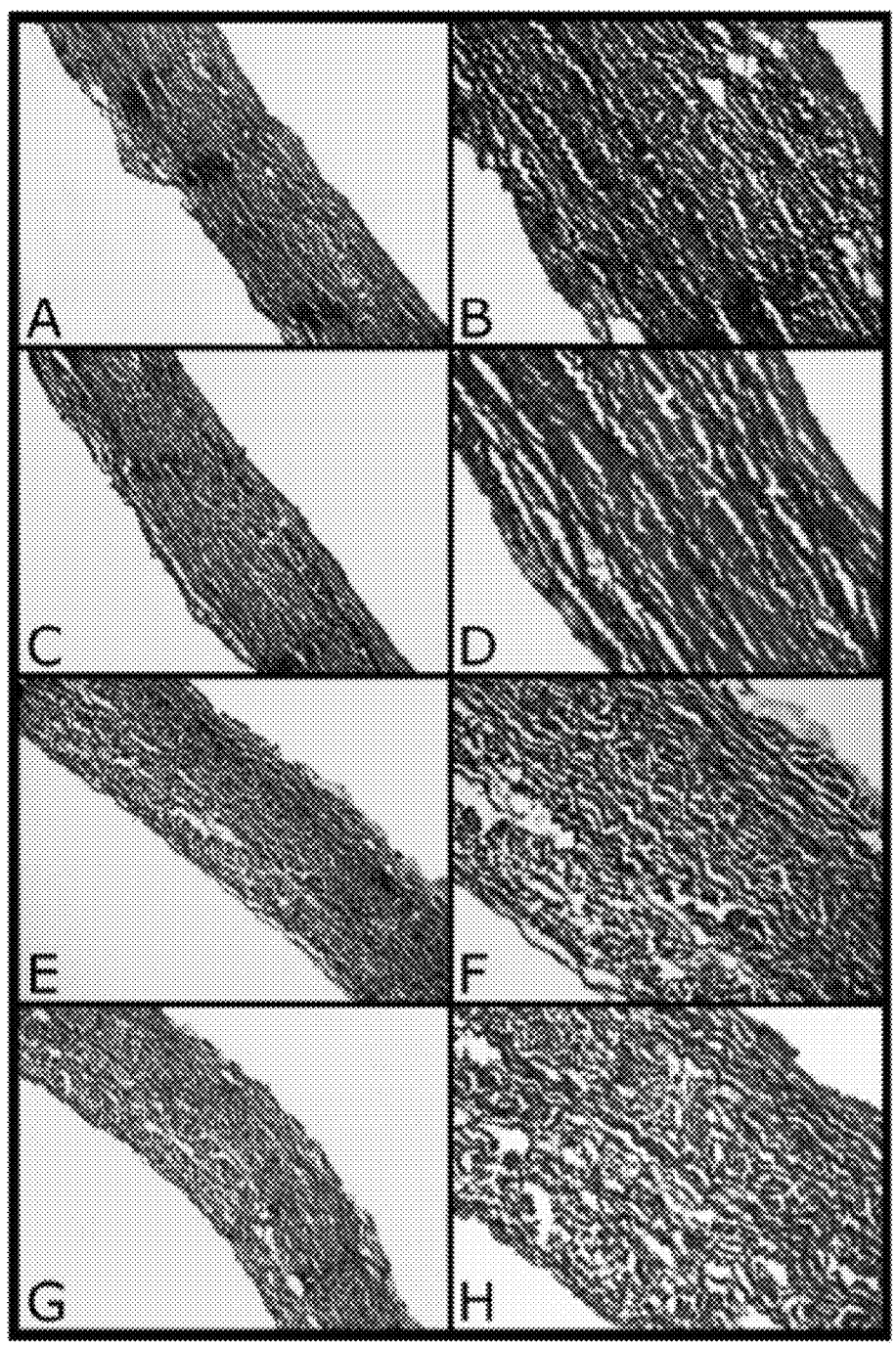
FIG. 19: Mallory Trichromic staining of FACTA™ treated commercial BHVs after 1 month follow-up in the swine. No significant presence of abnormal fibrous formation, like pannus or structured thrombi. In some samples is dearly evident the preservation of the elastic component (box E and F, G and H). Box A, C, E and G magnification 4×. Box B, D, F and H magnification 10×.

At the Mallory Trichromic staining, the FACTA™ treated commercial BHVs do not report the presence of any abnormal fibrous formation such as pannus or structured thrombus (FIG. 19). It is important to note the presence of pink/purple streaks inside the collagen matrix in some explanted samples (FIG. 19, box E and F, G and H), corresponding to the elastic fibers. Interestingly, such elastic fibers are never visible in the explants of untreated commercial BHVs.

Figure 20:
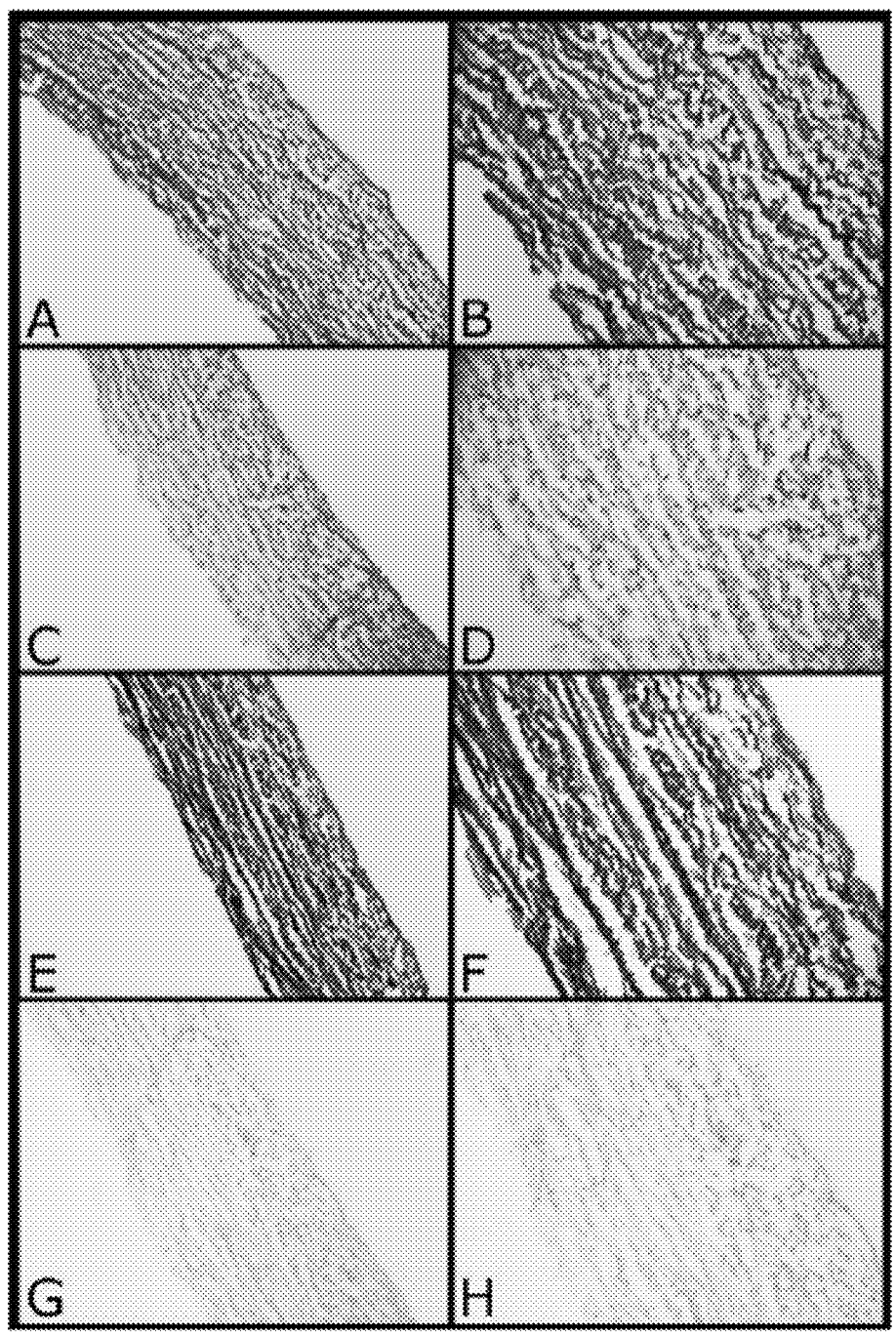
FIG. 20: staining of the reference commercial BHV (not implanted in the swine). H&E box A and B; Oil Red "O", box C and D; Mallory Trichromic, box E and F; Von Kossa, box G and H. Box A, C, E and G magnification 4×. Box B, D, F and H magnification 10×.

A commercial BHV, not implanted in the animal model, was histologically processed as a reference control. From the investigations emerge how this tissue does not show any foreign body reaction (FIG. 20, box A and B), and consequently, it is not affected by the development of fibrotic pannus or thrombi (FIG. 20, box E and F). There are also no lipid infiltrations or calcified deposits (FIG. 20, box C and D and G and H respectively). It should be noted that the elastic fibers are well represented by the Mallory staining (FIG. 20, box E and F), similar to that found for the FACTA™ treated commercial BHV (FIG. 19, box E and F, G and H).

Figure 21:
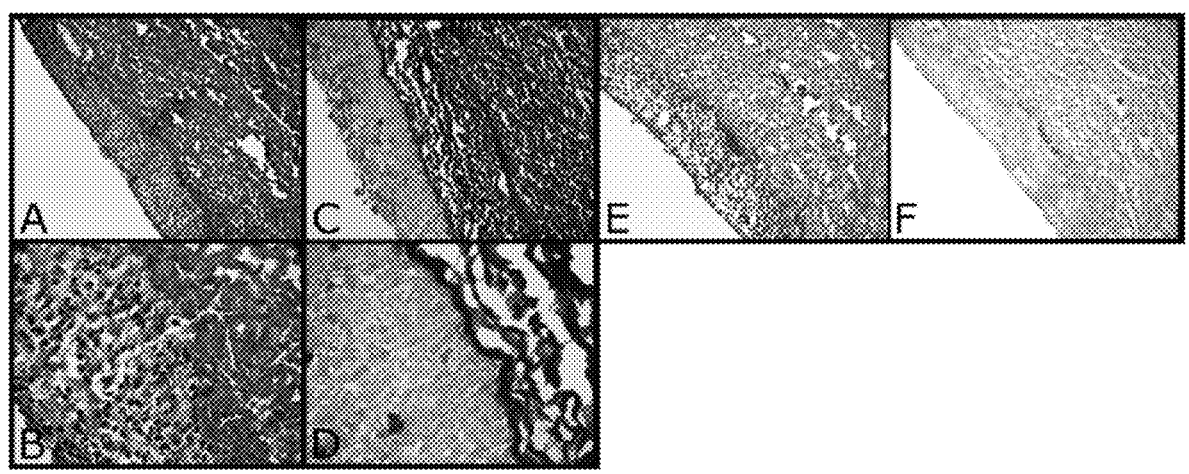
FIG. 21: multiple staining of FACTA™ treated commercial BHVs after 1 month follow-up in the swine. H&E box A and B; Mallory Trichromic, box C and D; Oil Red "O", box E; Von Kossa, box F. Box A, C, E and F magnification 4×. Box B and D, magnification 40×.

FIG. 21 shows a panel of different histological staining of a FACTA™ treated commercial BHVs. This panel summarizes all the improvements that the FACTA™ treatment provides to the bioprosthetic tissue. It is clearly evident the barrier effect exerted by the treatment; in fact, the host cellular population is unable to penetrate within the matrix (box B and D). This barrier effect is further confirmed by the absence of any lipid infiltration as showed in the box E. Finally, the tissue is free from calcific deposition (box F).

Resistance to Bacterial Adhesion

The anti-adhesive bacterial activity on FACTA™ treated and untreated commercial valves was evaluated with the bacterial species of *Staphylococcus aureus* ATCC 6538 (gram-positive). The bacteria were grown overnight in Tryptic Soy Broth (TSB) at of 37° C. The total bacterial load was assessed by 10-factor serial dilutions in TSB (10-1 to 10-7), sown in Petri dishes with appropriate selective medium (MSA-Mannitol Selective Agar) and kept in overnight incubator. At the end of the incubation, the units forming colony (UFC) were counted to determine the effective concentration of the microorganism. Furthermore, the value of optical density at 600 nm (OD600) was determined from each tiled dilution, in order to verify the linearity between the latter and the effective microbial load of the broth. Commercial FACTA™ treated and untreated BHVs leaflets were cut with a punch for biopsies (3 mm in diameter), in order to obtain the same useful surface for bacterial adhesion. The tissue punches thus obtained were washed with PBS and incubated overnight at room temperature in PBS+gentamicin (300 µg/mL) under moderate but constant agitation.

After overnight incubation, the commercial BHVs tissue punches were washed extensively in PBS to remove any remaining antibiotics. Subsequently, the FACTA™ treated and untreated samples were exposed to *S. aureus* bacterial suspensions (bacterial load $1 \times 10^7$ CFU/mL) for 90 minutes at room temperature under moderate but constant agitation. At the end of the incubation, the tissue samples were subject to three moderate vortexing mix to facilitate the detachment of the loosely bound bacteria.

Subsequently, the different tissue punches were homogenized by Ultraturrax and serial dilutions of the obtained homogenates, plated in Petri dishes containing the appropriate selective growth media. Finally, after 24 hours of incubation at 37° C., the colony-formed units were counted for each type of samples. The bacterial anti-adhesive activity was calculated using the following formula:

$$100 - \left[\left(\frac{CT}{CNT}\right) * 100\right]$$

Where CT is the bacterial charge of the tissue sample obtained from a commercial BHV treated with the FACTA™ technology and CNT is the one achieved in tissue pinches from commercial BHVs (untreated).

Figure 22:
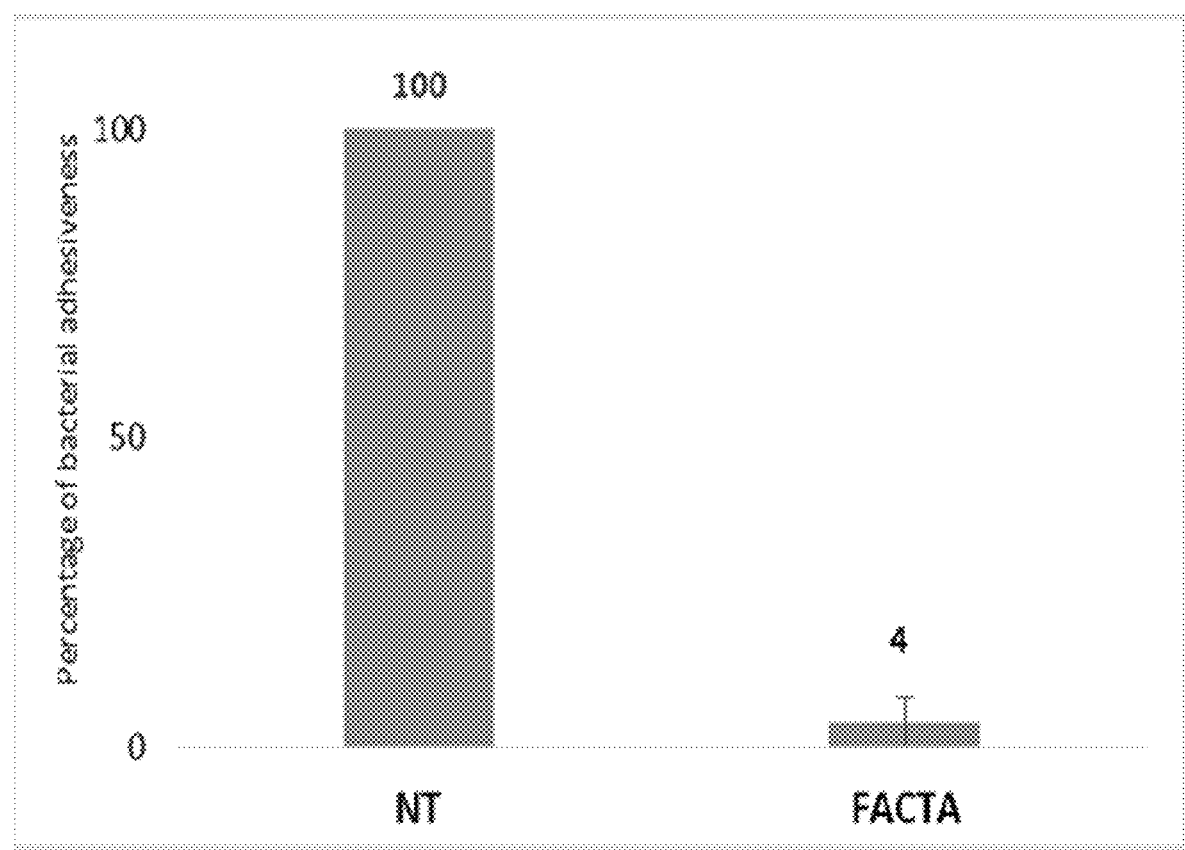
FIG. 22: shows the percentage of *S. aureus* adhesiveness on FACTA™ treated commercial BHVs leaflets compared to untreated leaflets (n=5 for each type of samples).

As shown in FIG. 22, the FACTA™ treatment significantly limits the adhesive capacity of *S. aureus* (reduction of 96±4%) on the tissue surface.

Calcification Mitigation Properties in Wild-Type Murine Animal Model

To evaluate the calcification mitigation properties of FACTA™ technologies, treated (F) and untreated (C) pericardial bioprosthetic heart valve (BHV) leaflets from Trifecta GT™ model (Abbott/St. Jude), were implanted subdermally in the back of C57Bl/6 wild-type mice. A total of 30 mice were enrolled, and each animal received a single specimen. Tissue samples were explanted after 1, 2 and 4 months of follow-up. As a control sample, calcium quantification was also carried out in off-the-shelves original Trifecta GT™ valve leaflets, labelled UN (unimplanted). Calcium content was evaluated by Inductive Coupled Plasma (ICP—a specific type of mass spectroscopy with a calcium quantification threshold of 0.048 µg/mg of tissue) and expressed as µg/mg of dry defatted weight (d.d.w.).

Figure 23:
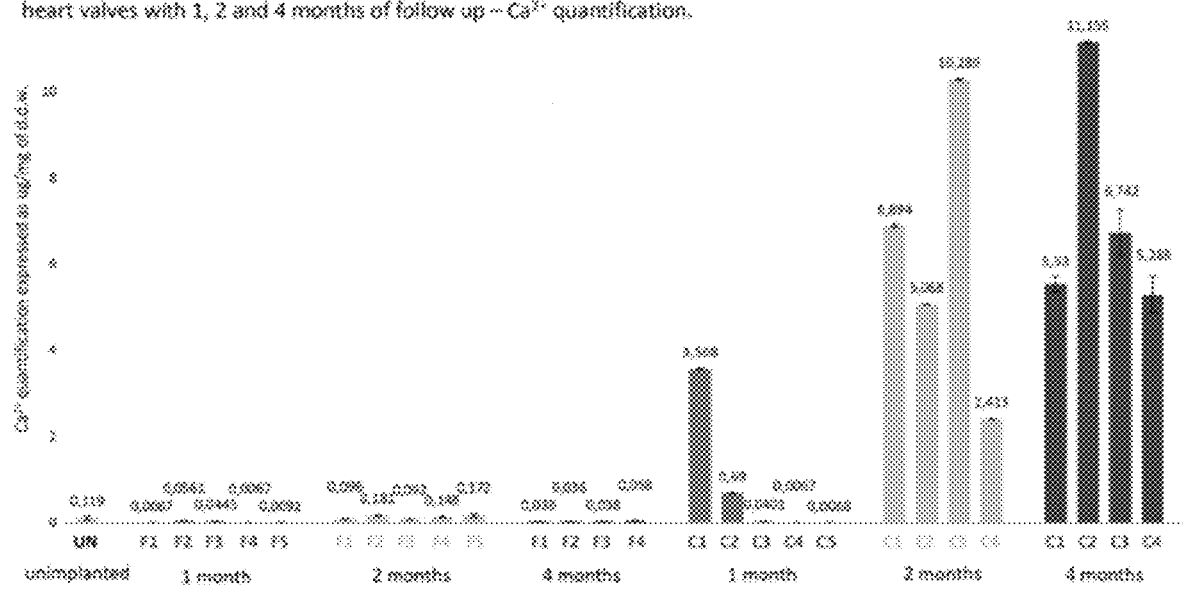
FIG. 23: results of the $Ca^{2+}$ quantification comparison (by ICP analysis) in FACTA™ treated (F) and untreated (C) leaflets from commercial bioprosthetic heart valve after 1, 2 and 4 months follow-up in the WT mice.

To further confirm the calcium quantification as carried on by ICP analysis, histological preparations of FACTA™ treated (F) and untreated (C) samples after 4 months of follow-up were performed. Histological preparations were analyzed by Von Kossa staining, a specific technique to highlight calcium deposition in biological tissues The results of the calcium quantification by ICP analysis are shown in FIG. 23.

The untreated original samples (C) showed a considerable tendency to calcify just after the first month of implantation. The trend continues significantly during the follow-up resulting in a calcium deposition of 7.17 µg/mg of d.d.w. as quantified at the end of the fourth month of the implant (Table 1). Conversely, the FACTA™ treated samples (F) report a negligible amount of calcium even after 4 months follow-up. Noteworthy, the calcium content in the F samples does not exceed significantly the total calcium detected in the UN, confirming no calcium uptake over time (Table 1).

TABLE 1

Average of calcium content expressed as µg/mg of d.d.w. in FACTA ™ treated (F) and untreated (C) samples after different follow-up.

| SAMPLE TYPE | 1 MONTH | 2 MONTHS | 4 MONTHS |
|---|---|---|---|
| FACTA ™ TREATED | 0.0246 ± 0.02 | 0.1378 ± 0.04 | 0.0425 ± 0.01 |
| UNTREATED | 0.8623 ± 1.501 | 6.166 ± 0.01 | 7.1787 ± 0.23 |
| UNIMPLANTED | 0.1192 ± 0.05 | | |

Figure 24:
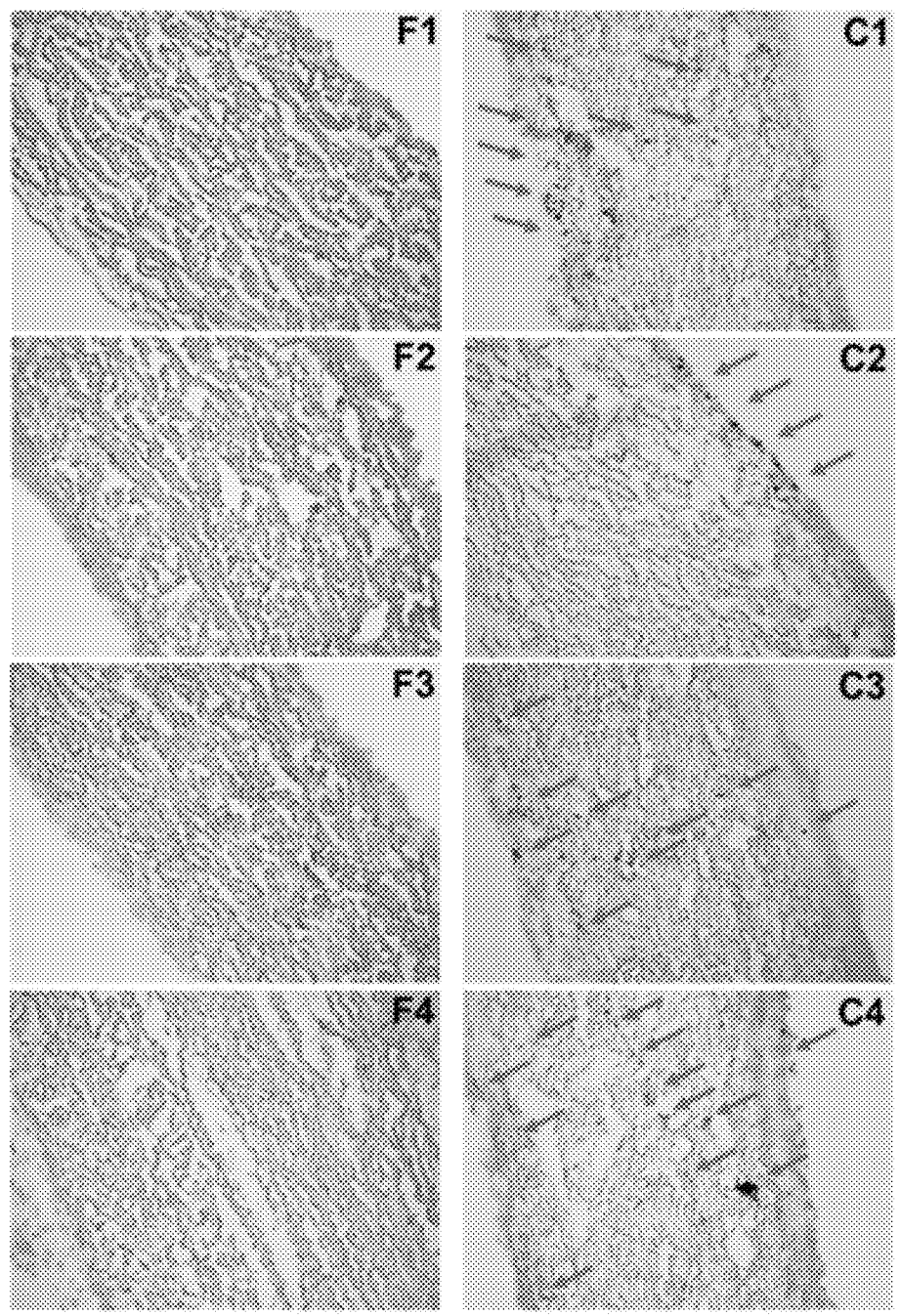
FIG. 24: results of the $Ca^{2+}$ quantification after Von Kossa histological staining on FACTA™ treated (F) and not treated (C) samples analysis after 4 months follow-up in the WT mice.

The results of the Von Kossa histological staining are shown in FIG. 24.

Calcium deposits are recognizable as black spots (indicated, where present, by the arrows). According to the ICP analysis, FACTA™ treated samples (F) do not exhibit any significant presence of calcium deposition after 4 months follow-up in the mice sub-cutis. On the other hand, original untreated control samples (C), report the presence of different calcium aggregates, some even of considerable dimension (C4 box).

Calcification Mitigation Properties in an Alpha-Gal Knockout Murine Animal Model The purpose of the test was the evaluation of the calcium uptake in leaflets excised from a commercially available Trifecta GT™ BHV and its FACTA™ treated counterparts, once implanted in an alpha-Gal knockout (KO) murine animal model. The KO mouse is a specifically developed BCI-owned murine model genetically modified to silence the expression of the alpha-Gal xenoantigen. Alpha-Gal KO mice are characterized by having an immunological response mechanism similar to the human where the alpha-Gal antigen stimulates the production of specific anti-Gal antibodies. Leaflets were implanted sub-cutis in the back of C57Bl/6 alpha-Gal KO mice.

Calcium content was evaluated by Inductive Coupled Plasma (ICP—a specific type of mass spectroscopy) and expressed as µg/mg of dry defatted weight (d.d.w.). FACTA™ treated (F) and original leaflets (C), excised from commercial Trifecta GT valves (Abbott/St. Jude), were implanted subdermally in the back of wild type (WT) and knock-out (KO) for alpha-Gal mice. Each animal received a single specimen.

As a control sample, calcium quantification was also carried out in off-the-shelves original TRIFECTA GT™ valve leaflets, labelled UN (uninmplanted).

Figure 25:
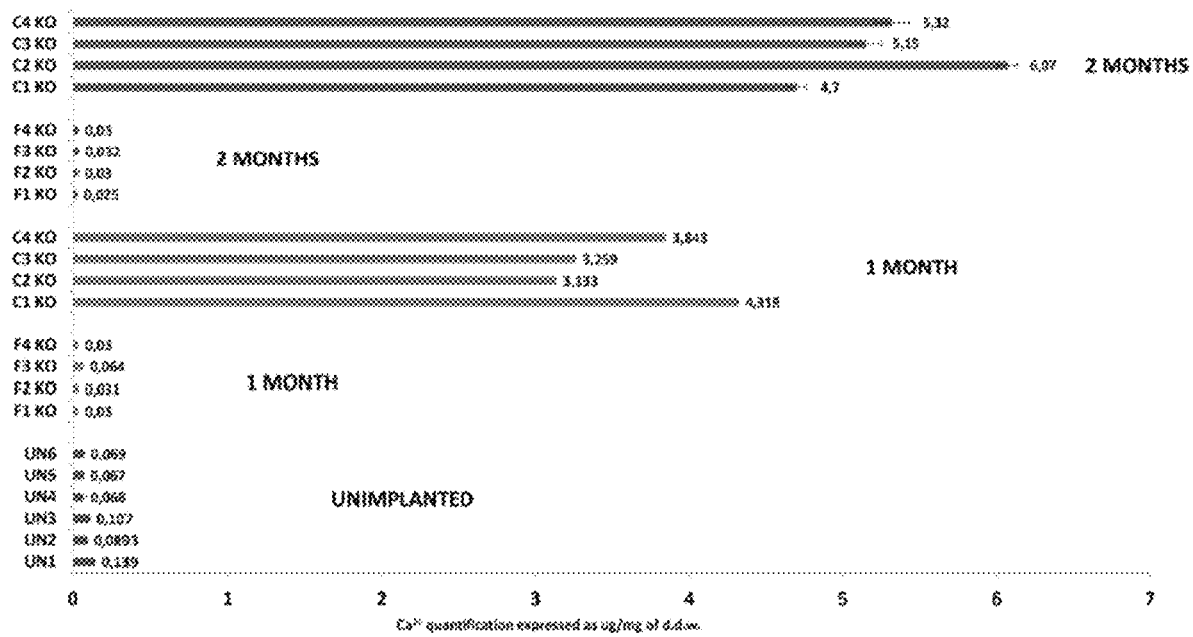
FIG. 25: results of the $Ca^{2+}$ quantification comparison (by ICP analysis) in FACTA™ treated (F) and untreated (C) leaflets from commercial bioprosthetic heart valve leaflets after 1 and 2 months of follow-up in alpha-Gal KO mice.

The results are shown in FIG. 25.

The amount of calcium determined in the F samples at 1-month as well as 2-months of follow-up was negligible as it is lower than the ICP quantification threshold (0.048 µg/mg). The calcium content detected in the F samples does not exceed the total calcium detected in the UN, confirming no calcium uptake at 1 and 2 months follow-up. Conversely, the C specimens implanted in KO show a pro-calcific effect by reporting a significant and homogenous presence of calcium.

The results demonstrate a clear role of the alpha-Gal in promoting calcium deposition in the KO mice as it happens into humans.

FACTA™ treatment proves to be effective in counteracting the calcification even in a critical physiological system like the alpha-Gal KO model.

From the above disclosure, the advantages offered by the present invention will be immediately evident to the person skilled in the art.

For instance, the invention method is capable of limiting the deposition of calcium salts, therefore preventing the formation of episodes of calcific dystrophy of the valve.

Also, the invention method has shown to protect the treated cardiovascular bio-prostheses against the formation of blood clots and structured thrombi.

The method of the invention allows to avoid the lipoproteins infiltration from blood circulation and the consequent onset of cell-mediated inflammatory tissue response in the treated cardiovascular bio-prostheses.

Finally, with the invention a method has been developed to avoid colonization by bacteria, preserving the cardiovascular tissues from the onset of the endocarditis.

The method disclosed in the present invention proved to be very stable and safe.

The collected evidence show that it did not significantly alter the hydrodynamic and biomechanical integrity of the treated valves. Nevertheless, the values of the hydrodynamic parameters obtained for the treated valves range within the values indicated in the ISO 5840-3 standard.

Also, the method proved to be able to inhibit the formation of calcified deposits both at the in-vitro and in-vivo investigations. The BHVs treated with FACTA™ were clearly non-thrombogenic and protected from cellular and lipid infiltration.

Last but not least, with the invention a method has been devised that can be carried out with conventional devices and machines.

As for the invention kit, it is aimed at the autonomous treatment of bioprosthetic substitutes that are already prepared, with a method according to the invention as described above, useful for health facilities like clinics and hospitals.

The invention is susceptible of numerous modifications and variations, all of which are within the scope of the appended claims.

Moreover, all the elements may be substituted by other, technically equivalent elements.

The invention claimed is:

1. A method for preventing the formation of calcified deposits on or inside an isolated biological matrix after said isolated biological matrix is implanted in a body, wherein the method comprises the step of:
   contacting a biological matrix with a solution comprising an effective amount of a mixture of phenolic compounds to obtain said isolated biological matrix; and
   implanting in the body said isolated biological matrix, wherein said isolated biological matrix comprises no calcified deposits on or inside said isolated biological matrix after said isolated biological matrix is implanted in the body for a period of at least 2 months.

2. The method according to claim 1, wherein said contacting is performed for a period of less than two hours at the temperature of 35±2° C. in the dark.

3. The method according to claim 1, wherein said mixture of phenolic compounds comprises a mixture of phenylpropanoids selected from the group consisting of: phenols, phenolic aldehydes, phenolic acids, phenylamines, phenol compounds, flavonoids, phenylpropanoids, and tannins.

4. The method according to claim 1, wherein said mixture of phenolic compounds comprises a mixture of phenylpropanoids selected from the group consisting of: resveratrol, aloin, cyanarin, epigallocatechin, tannic acid, caffeic acid, chlorogenic acid, hydroxytyrosol, rosmarinic acid, naringenin, gallic acid, hesperidin, quinic acid, eleonolic acid, pinoresinol, luteolin, apigenin, tangeritin, isorhamnetin, kaempferol, myricetin, eriodictyol, hesperetin, naringenin, theaflavin, thearubigins, daidzein, genistein, glycitein, pterostilbene, delphinidin, malvidin, pelargonidin, peonidin, chicoric acid, ferulic acid, and salicylic acid.

5. The method according to claim 1, wherein the solution further includes a suitable buffer.

6. The method according to claim 3, wherein within the solution each phenylpropanoid is comprised in a concentration of about 0.2-5 mg/ml.

7. The method according to claim 1, wherein said solution comprises one of the following combinations of phenylpropanoids (Compound 1 and Compound 2):

| Compound 1 - quantity (mg/ml) ± 0.5 mg/ml | Compound 2 - quantity (mg/ml) ± 0.5 mg/ml |
|---|---|
| Resveratrol 3 mg/ml | Aloin 1.5 mg/ml |
| Resveratrol 3 mg/ml | Cynarin 2 mg/ml |
| Epigallocatechin 2 mg/ml | Aloin 1.5 mg/ml |
| Tannic Acid 4 mg/ml | Chlorogenic Acid 4 mg/ml |
| Tannic Acid 4 mg/ml | Caffeic Acid 2 mg/ml |
| Chlorogenic Acid 4 mg/ml | Hydroxytyrosol 4 mg/ml |
| Rosmarinic Acid 2.5 mg/ml | Aloin 1.5 mg/ml |
| Naringenin 1 mg/ml | Gallic Acid 1.5 mg/ml |
| Hesperetin 2 mg/ml | Gallic Acid 1.5 mg/ml. |

8. The method according to claim 1, wherein said isolated biological matrix is selected from the group consisting of vessels, cardiac valves, tendons, ligaments, pericardium, muscular fasciae, dura mater, tympanic membrane, intestinal submucosa, cartilages, adipose tissue, bone tissue, pelvic, abdominal, or breast tissue, and cardiovascular prostheses comprising one of cardiac valves and pericardial tissue patches.

9. The method according to claim 8, wherein said isolated biological matrix is a trans-catheter valve implantation (TAVI) prostheses or surgical valve prostheses.

10. The method according to claim 1, wherein the method provides one or more of: inactivating xenoantigens in biological matrixes, preventing the thrombus formation on or inside said biological matrix, preventing the lipid infiltration into a biological matrix, preventing the onset of inflammatory process mediated by the cellular component, and preventing the biofouling processes on a biological matrix.

11. An isolated biological matrix obtained according to the method of claim 1.

12. An isolated biological matrix obtained according to the method of claim 1 for use in the treatment of heart diseases in the medical, biomedical and/or veterinary field.

13. The isolated biological matrix according to claim 12, wherein said isolated biological matrix is a trans-catheter valve implantation (TAVI) prostheses or surgical valve prostheses.

14. A method for the treatment of heart diseases in humans or animals comprising applying to the humans or the animals an isolated biological matrix obtained according to the method of claim 1.

15. The method for the treatment of heart diseases in humans or animals according to claim 14, wherein said biological matrix is a trans-catheter valve implantation (TAVI) prostheses or surgical valve prostheses.

16. A kit for performing the method of claim 1, comprising:
a container containing a suitable buffer,
a container containing an effective amount of a solution of claim 1 to be mixed with said buffer,
one or more additional containers containing washing buffers, and
an instruction booklet containing the description of the timings and modes for performing said method.

17. A method for preventing the formation of calcified deposits on or inside an isolated biological matrix, the method comprising a step of contacting for a period of less than two hours at the temperature of 35±2° C. in the dark a biological matrix with a solution comprising the following effective combinations of phenylpropanoids (Compound 1 and Compound 2) to obtain said isolated biological matrix:

| Compound 1 - quantity (mg/ml) ± 0.5 mg/ml | Compound 2 - quantity (mg/ml) ± 0.5 mg/ml |
|---|---|
| Resveratrol 3 mg/ml | Aloin 1.5 mg/ml |
| Resveratrol 3 mg/ml | Cynarin 2 mg/ml |
| Epigallocatechin 2 mg/ml | Aloin 1.5 mg/ml |
| Tannic Acid 4 mg/ml | Chlorogenic Acid 4 mg/ml |
| Tannic Acid 4 mg/ml | Caffeic Acid 2 mg/ml |
| Chlorogenic Acid 4 mg/ml | Hydroxytyrosol 4 mg/ml |
| Rosmarinic Acid 2.5 mg/ml | Aloin 1.5 mg/ml |
| Naringenin 1 mg/ml | Gallic Acid 1.5 mg/ml |
| Hesperetin 2 mg/ml | Gallic Acid 1.5 mg/ml; | and
implanting in a body said isolated biological matrix, wherein said isolated biological matrix comprises no calcified deposits on or inside said isolated biological matrix after implantation of said isolated biological matrix in the body for a period of at least 2 months.

* * * * *